(12) United States Patent
Cummins et al.

(10) Patent No.: US 10,582,955 B2
(45) Date of Patent: Mar. 10, 2020

(54) METHODS OF IMPLANTING BONE PLATE ASSEMBLIES

(71) Applicant: ZAVATION MEDICAL PRODUCTS LLC, Flowood, MS (US)

(72) Inventors: John Franklin Cummins, Kosciusko, MS (US); John Lawrence Walker, Madison, MS (US); Eric Graham, Oceans Springs, MS (US)

(73) Assignee: Zavation, LLC, Flowood, MS (US)

( * ) Notice: Subject to any disclaimer, the term of this patent is extended or adjusted under 35 U.S.C. 154(b) by 121 days.

(21) Appl. No.: 15/927,440

(22) Filed: Mar. 21, 2018

(65) Prior Publication Data
US 2018/0310965 A1 Nov. 1, 2018

Related U.S. Application Data

(60) Provisional application No. 62/545,127, filed on Aug. 14, 2017, provisional application No. 62/512,986, filed on May 31, 2017, provisional application No. 62/474,768, filed on Mar. 22, 2017.

(51) Int. Cl.
| | | |
|---|---|---|
| A61B 17/88 | (2006.01) | |
| A61B 17/70 | (2006.01) | |
| A61B 17/80 | (2006.01) | |
| A61B 17/68 | (2006.01) | |
| A61B 17/56 | (2006.01) | |

(52) U.S. Cl.
CPC ...... *A61B 17/7059* (2013.01); *A61B 17/7076* (2013.01); *A61B 17/7077* (2013.01); *A61B 17/808* (2013.01); *A61B 17/8023* (2013.01); *A61B 17/8897* (2013.01); *A61B 17/8042* (2013.01); *A61B 2017/564* (2013.01); *A61B 2017/681* (2013.01)

(58) Field of Classification Search
CPC ............ A61B 17/7059; A61B 17/7076; A61B 17/8897; A61B 2017/564; A61B 2017/681
USPC ... 606/279, 280, 70, 71, 281, 282, 284, 286, 606/289, 295, 296, 297, 90, 96, 99, 104, 606/105, 86 B
See application file for complete search history.

(56) References Cited

U.S. PATENT DOCUMENTS

| | | | | |
|---|---|---|---|---|
| 6,066,142 A | * | 5/2000 | Serbousek | A61B 17/1728 606/70 |
| 6,402,756 B1 | | 6/2002 | Ralph et al. | |
| 7,416,553 B2 | * | 8/2008 | Patel | A61B 17/1757 606/246 |
| 7,862,597 B2 | * | 1/2011 | Gause | A61B 17/1728 606/290 |
| 9,028,498 B2 | * | 5/2015 | Hershgold | A61B 17/7059 606/71 |
| 9,101,422 B2 | | 8/2015 | Freid et al. | |
| 9,486,250 B2 | * | 11/2016 | Altarac | A61B 17/7059 |
| 2005/0015093 A1 | * | 1/2005 | Suh | A61B 17/1728 606/96 |
| 2005/0021040 A1 | * | 1/2005 | Bertagnoli | A61B 17/025 606/90 |
| 2012/0083846 A1 | | 4/2012 | Wallenstein et al. | |
| 2012/0158059 A1 | | 6/2012 | Freid et al. | |
| 2016/0051297 A1 | * | 2/2016 | Steffensmeier | A61B 17/808 606/86 B |

(Continued)

*Primary Examiner* — Pedro Philogene
*Assistant Examiner* — David C Comstock
(74) *Attorney, Agent, or Firm* — Olive Law Group, PLLC

(57) ABSTRACT

Methods of installing bone plates on adjacent vertebrae are provided.

15 Claims, 29 Drawing Sheets

(56) References Cited

U.S. PATENT DOCUMENTS

2018/0085105 A1\* 3/2018 Kim .................. A61B 17/0206

\* cited by examiner

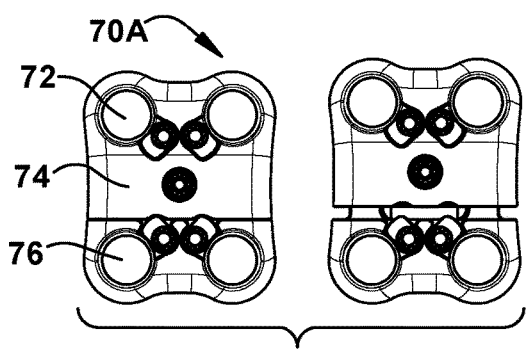
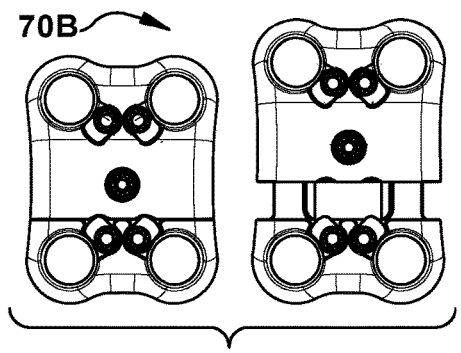
FIG. 12A
FIG. 12B
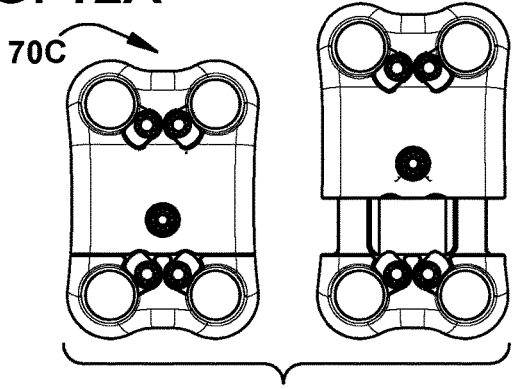
FIG. 12C
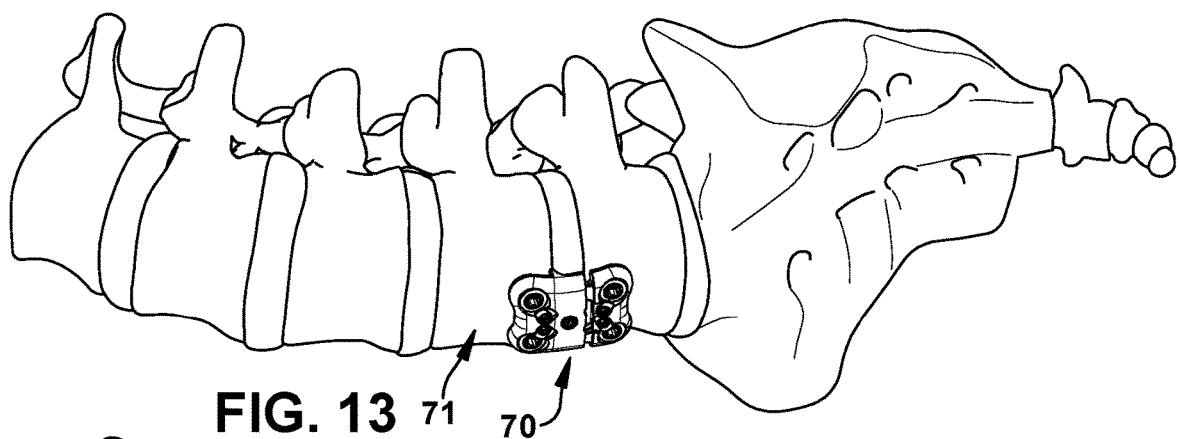
FIG. 13
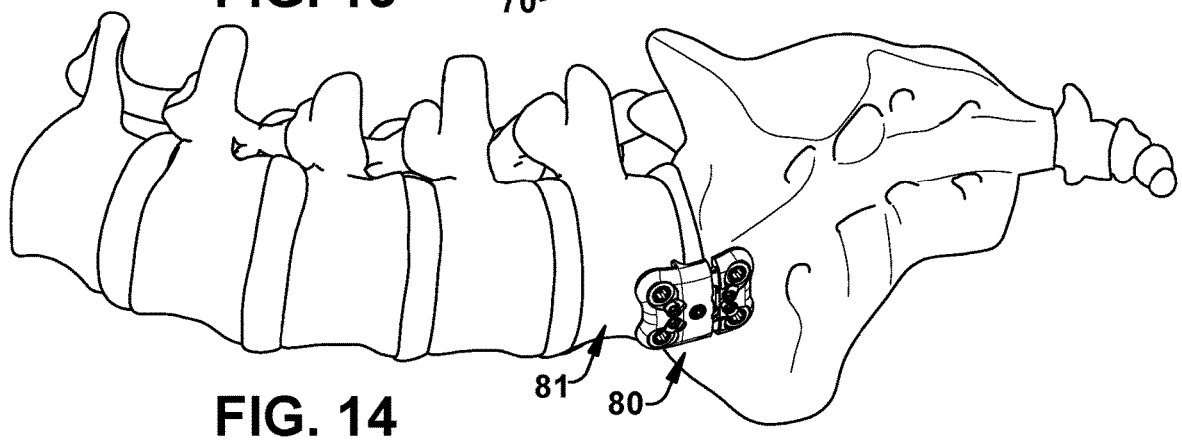
FIG. 14

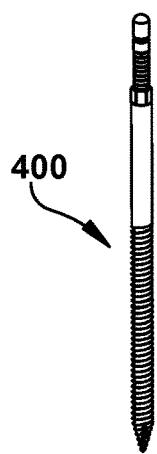
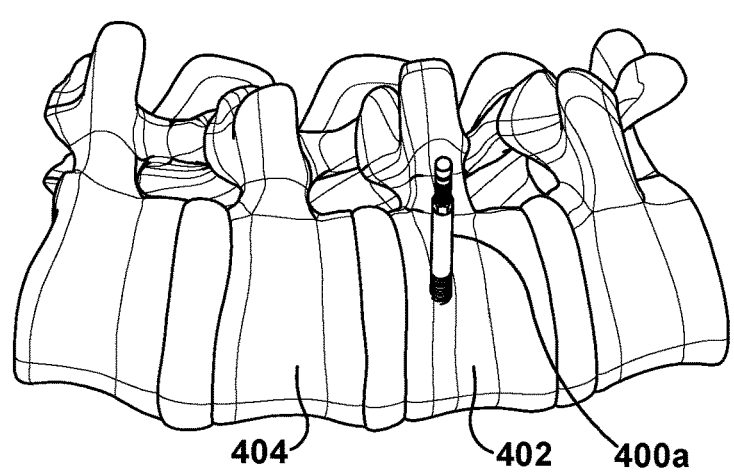
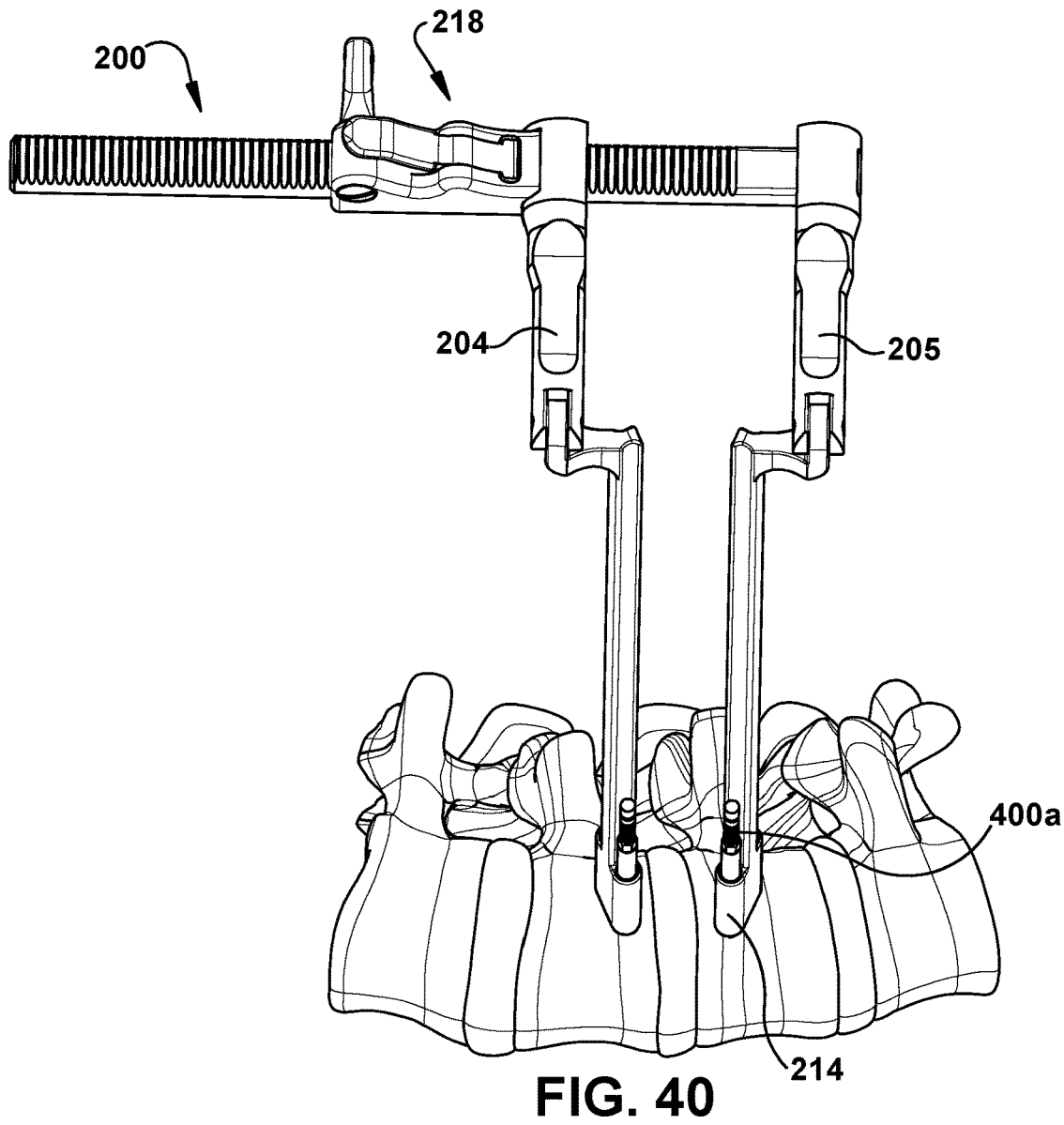
FIG. 38
FIG. 39
FIG. 40

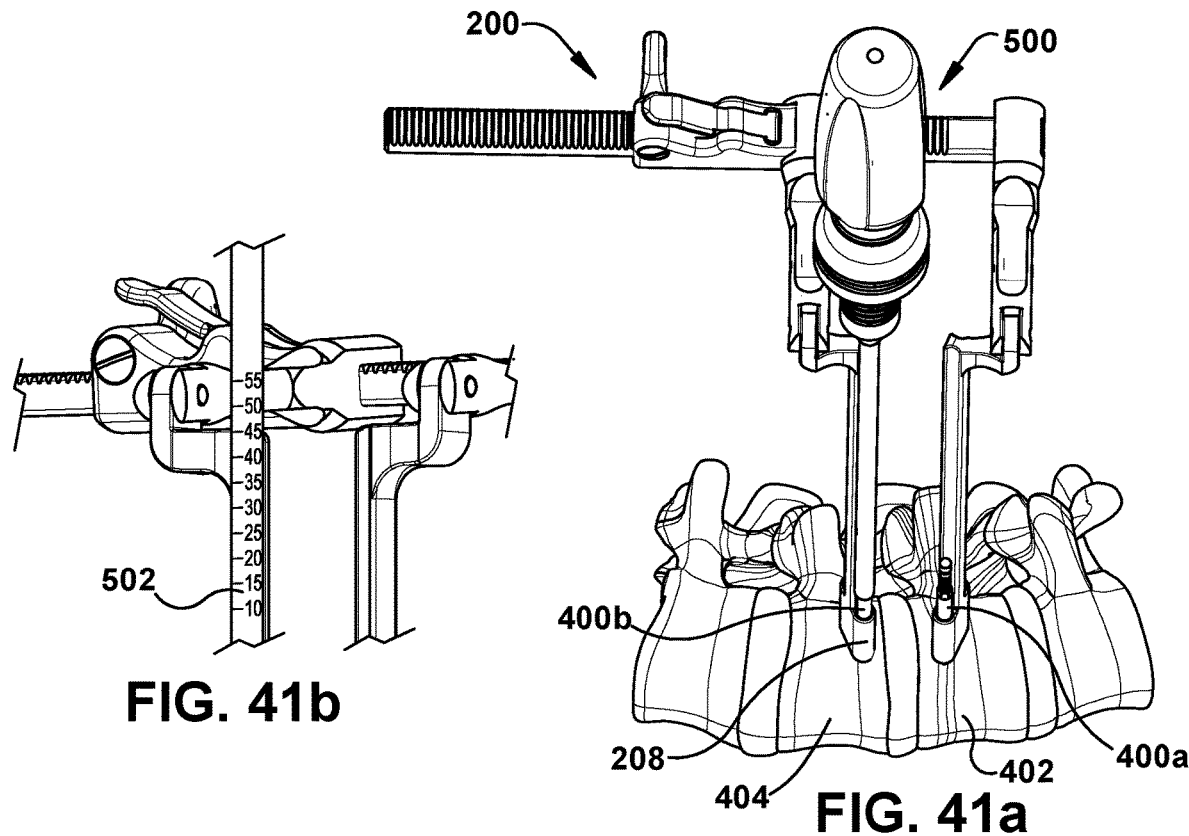
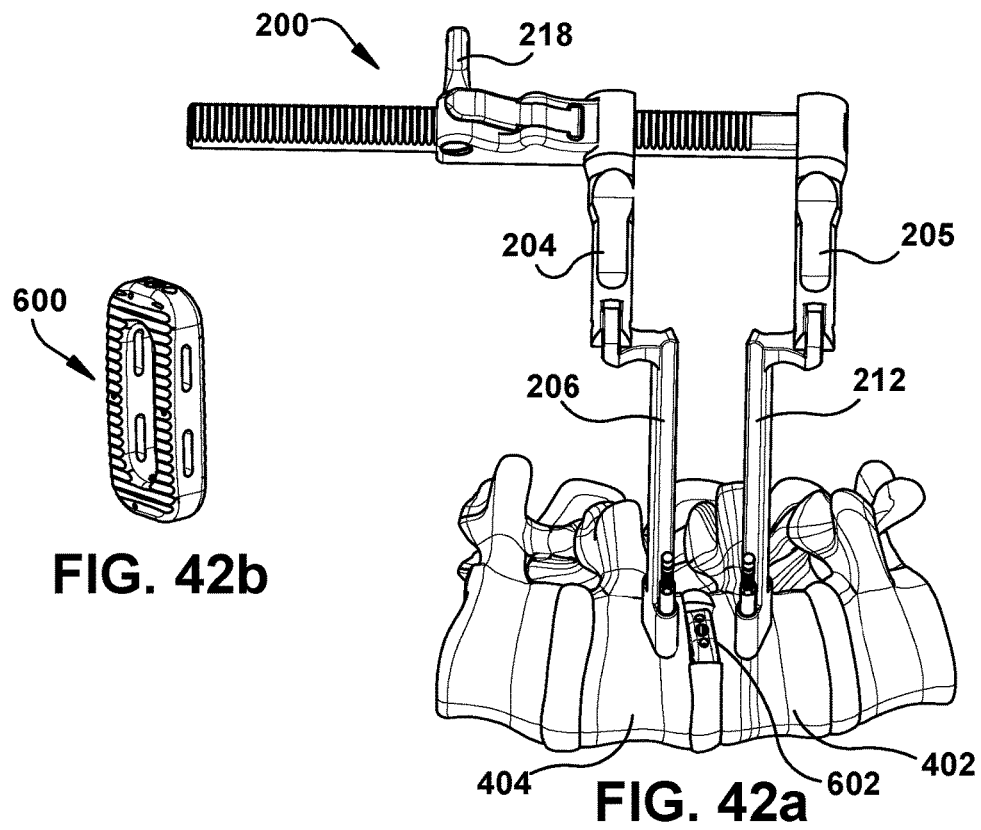

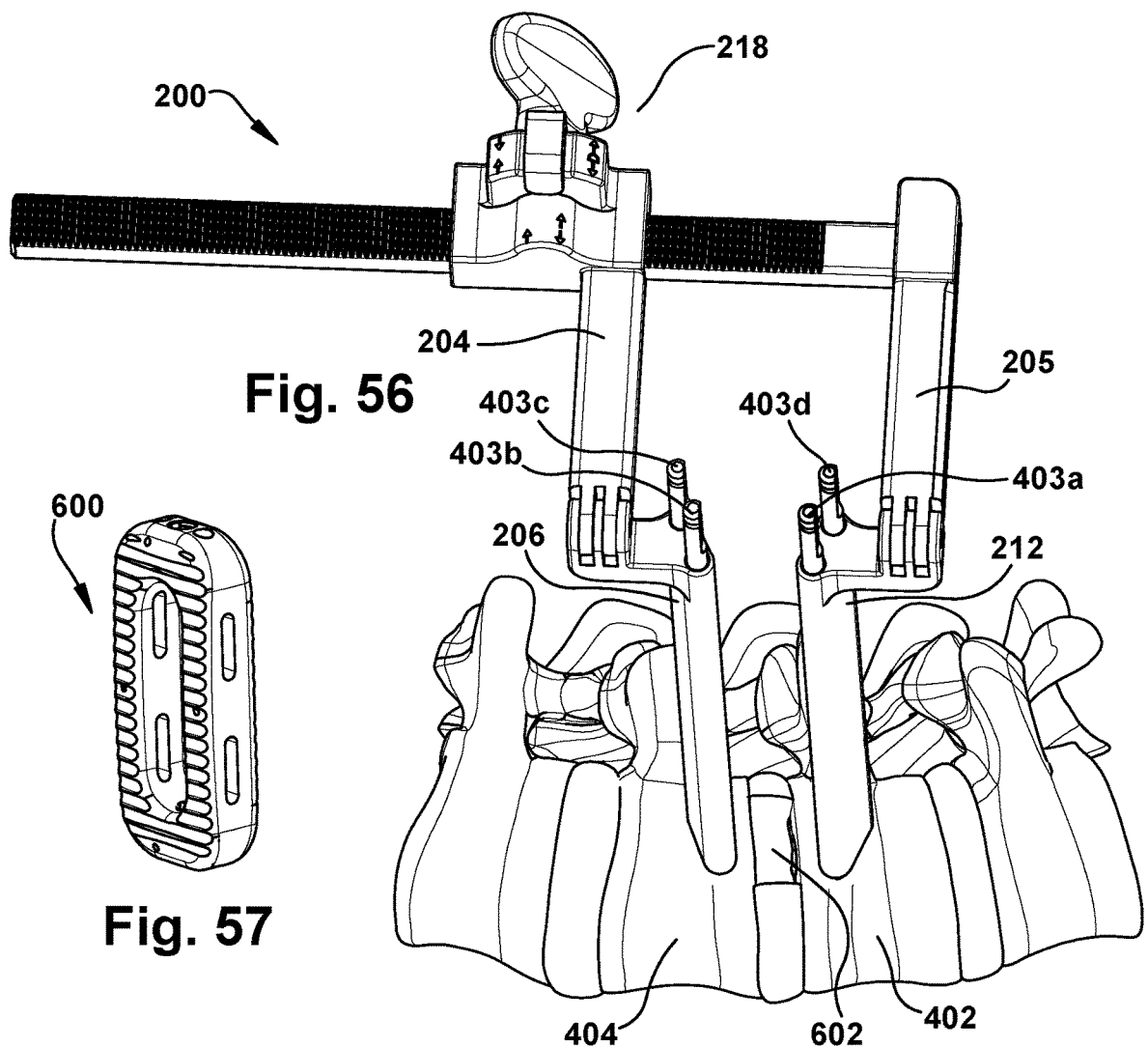
Fig. 56
Fig. 57
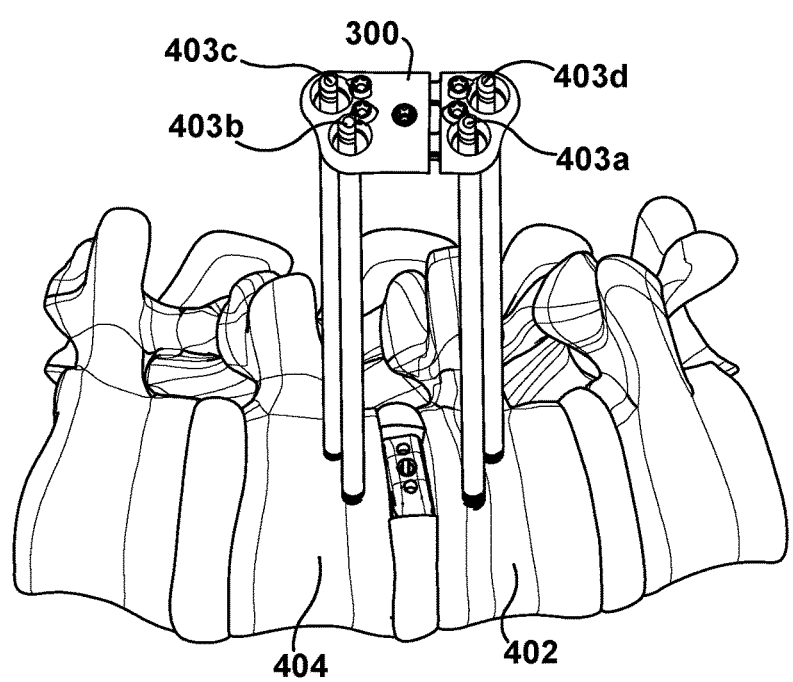
Fig. 58

METHODS OF IMPLANTING BONE PLATE ASSEMBLIES

RELATED APPLICATIONS

This application claims priority to U.S. Provisional Application No. 62/545,127 filed on Aug. 14, 2017; U.S. Provisional Application No. 62/474,768, filed on Mar. 22, 2017; and U.S. Provisional Application No. 62/512,986 filed on May 31, 2017. All applications are incorporated by reference herein in their entirety.

TECHNICAL FIELD

The present disclosure relates to methods of installing bone plate assemblies.

BACKGROUND

Internal fixation devices, such as plates, pins, rods, wires and screws, are often used to stabilize and join bones. For example, a bone plate can be used to facilitate healing of bone fractures or to fuse adjacent vertebral bodies of a patient's spinal column. The plate is placed against adjacent bone tissue and screws are inserted through screw holes of the plate into the adjacent bone tissue to anchor the plate into proper position.

Many bone plates are of fixed height or expandable. Fixed bone plates are manufactured in various heights so that one plate can be selected to best fit adjacent bone tissue. Alternatively, an expandable bone plate has an adjustable height to maintain spacing of the vertebrae above and below the removed vertebral or disc material. Both types of bone plates have limitations and problems. Fixed bone plates have good structural integrity but can be cumbersome to place. Further, the fixed bone plate must be exactly the correct height. If the bone plate is too large, it can cause over distraction to the vertebral bodies or damage the vertebral body above and below the bone plate. If the bone plate is too small, it can displace out of position. Expandable bone plates are much easier to correctly size and place. However, the mechanical mechanism used to expand the bone plate may fail after implantation. The interconnection between components of an expandable bone plate should be secure enough such that the bone plate does not disassemble prior to or after implantation.

SUMMARY

The present disclosure relates to bone plate assemblies and method of installing the same. In an embodiment, a method of implanting an expandable bone plate against adjacent first and second vertebrae is provided. The method comprises obtaining an expandable bone plate comprising a first plate portion slidably attached to a second plate portion. The first and second plate portions collectively comprise a plurality of bone screw holes. The method further includes inserting a plurality of guide pins into a first vertebra and a second vertebra and distracting the space between the first vertebra and the second vertebra. The method also includes adjusting the size of the expandable plate, if necessary, so that the plurality of bone screw holes of the first and second plate portions are aligned with the plurality of guide pins. The method further comprises placing the plurality of bone screw holes about respective ones of the plurality of guide pins and seating the expandable bone plate against the first vertebra and the second vertebra. The method also includes removing the plurality of guide pins from the first vertebra and the second vertebra; and inserting a bone screw into each of the plurality of bone screw holes of the first and the second plate portions.

In another embodiment, the present invention provides a method of implanting an expandable bone plate against adjacent first and second vertebrae. The method comprises inserting one of a plurality of guide pins into a desired location of a first vertebra. The method further comprises obtaining an orthopedic instrument comprising a first guide and a second guide, each guide having a plurality of cannulas. The method also includes placing one of the cannulas of the first or second guide about the one of the plurality of guide pins. The method further includes adjusting the orthopedic instrument to adjust the relative position of the first and second guides to set the location of the remaining ones of the plurality of guide pins for insertion into the first vertebra and a second vertebra. The method also comprises inserting the remaining ones of the plurality of guide pins into the respective remaining ones of the plurality of cannulas of the first and second guide and into locations of the first vertebra and the second vertebrae. The method further comprises distracting the disc space between the first vertebra and the second vertebra and inserting an interbody device into the disc space. The method additionally comprises removing the orthopedic instrument. The method also includes obtaining an expandable bone plate comprising a first plate portion slidably attached to a second plate portion. The first and second plate portions collectively comprise a plurality of bone screw holes. The expandable bone plate further comprising a locking screw mounted on the first plate portion. The method includes adjusting the size of the expandable bone plate, if necessary, so that the plurality of bone screw holes of the first and second plate portions are aligned with the plurality of guide pins. The method also comprises placing the plurality of bone screw holes about respective ones of the plurality of guide pins. The method further includes removing the plurality of guide pins and inserting a bone screw through each of the plurality of bone screw holes of the expandable bone plate and through the holes created by the plurality of guide pins to seat the expandable bone plate against the first vertebra and the second vertebra.

In another embodiment, the present invention comprises a method of implanting an expandable bone plate against adjacent first and second vertebra comprising inserting one of a plurality of guide pins into a desired location of a first vertebra. The method further includes obtaining an orthopedic instrument comprising a first guide and a second guide, each guide having a plurality of cannulas. The method also includes aligning the first and second guides of the orthopedic instrument so that one of the cannulas of the first or second guide is disposed about the one of the plurality of guide pins and a distal end of the orthopedic instrument is contacting the first vertebra and a second vertebra. The method further includes inserting the remaining ones of the plurality of guide pins into the respective remaining ones of the plurality of cannulas of the first and second guide and into locations of the first vertebra and the second vertebrae. The method also includes distracting the disc space between the first vertebra and a second vertebra and inserting an interbody device into the disc space. The method includes removing the orthopedic instrument. The method also includes obtaining an expandable bone plate comprising a first plate portion slidably attached to a second plate portion. The first and second plate portions collectively comprising a plurality of bone screw holes. The expandable bone plate further comprises a locking screw mounted on the first plate portion. The method further includes adjusting the size of the expandable bone plate, if necessary, so that the plurality of bone screw holes of the first and second plate portions are aligned with the plurality of guide pins. The method also includes placing the plurality of bone screw holes about respective ones of the plurality of guide pins. The method further includes removing the plurality of guide pins and inserting a bone screw through each of the plurality of bone screw holes of the expandable bone plate and through the holes created by the plurality of guide pins to seat the expandable bone plate against the first vertebra and the second vertebra.

In another embodiment, a method of implanting a bone plate against a first vertebra and a second vertebra is provided. The method comprises obtaining an orthopedic instrument. The orthopedic instrument comprises a guide comprising a first guide portion and a second guide portion. The first guide portion comprises an anterior cannula and a posterior cannula. The second guide portion also comprises an anterior cannula and a posterior cannula. The orthopedic instrument further includes an expandable plate template attached to the distal end of the guide. The expandable plate template comprises a first plate template portion comprising an anterior hole axially aligned with and in fluid communication with the anterior cannula of the first guide portion and a posterior hole axially aligned with and in fluid communication with the posterior cannula of the first guide portion. The expandable plate template also includes a second plate template portion slidably attached to the first plate template portion and comprising an anterior hole axially aligned with and in fluid communication with the anterior cannula of the second guide portion and a posterior hole axially aligned with and in fluid communication with the posterior cannula of the second guide portion. The orthopedic instrument further includes a handle extending proximally from the expandable plate template. The method further includes placing the expandable plate template against a first vertebra. The method also includes inserting respective ones of a plurality of guide pins into the anterior cannula and the posterior cannula of the second guide portion into the first vertebra. The method further comprises sliding the first plate template portion away from the second plate template portion to set the location of insertion of additional guide pins in the first vertebra and the second vertebra. The method further includes inserting respective ones of the additional guide pins into the anterior cannula and the posterior cannula of the first guide portion into the second vertebra. The method also includes removing the orthopedic instrument from the first and the second vertebra leaving the plurality of guide pins in the first vertebra and the second vertebra. The method further comprises sliding an expandable plate over the plurality of guide pins to seat the expandable plate against the first and the second vertebra. The method further includes removing the plurality of guide pins.

BRIEF DESCRIPTION OF THE DRAWINGS

FIGS. 12A-12C are front views of a kit including expandable anterior lumbar and/or anterior sacrum bone plate assemblies according to an embodiment of the present invention illustrating such assemblies in a non-expanded position and a fully expanded position.

FIG. 13 is a perspective view of an expandable anterior lumbar bone plate assembly implanted on an anterior lumbar spinal region.

FIG. 14 is a perspective view of an expandable anterior sacrum bone plate assembly implanted on an anterior sacrum spinal region.

FIGS. 33-70 are schematic illustrations depicting devices and steps of methods for implanting an expandable bone plate assembly according to embodiments of the present disclosure.

DETAILED DESCRIPTION

Figure 1:
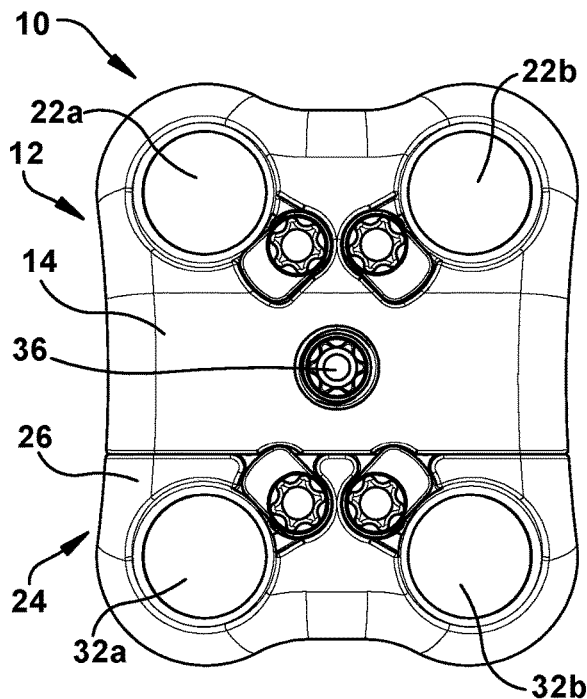
FIG. 1 is a front view of an expandable bone plate assembly according to an embodiment of the present disclosure.
Figure 2:
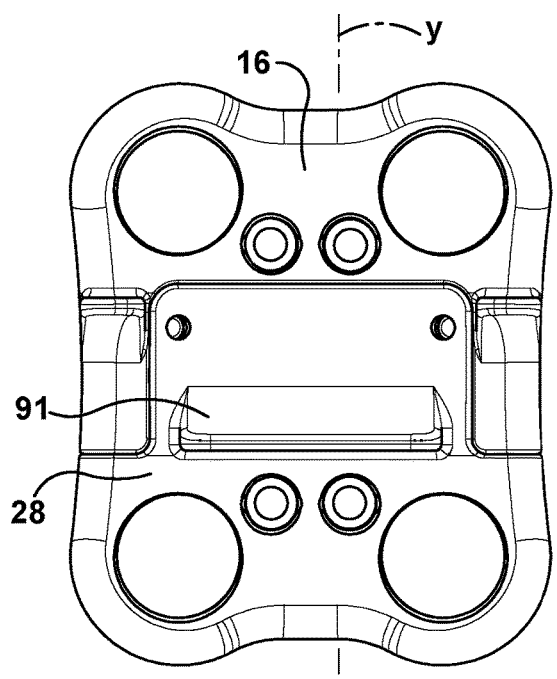
FIG. 2 is a back view of an expandable bone plate assembly according to an embodiment of the present disclosure.
Figure 7:
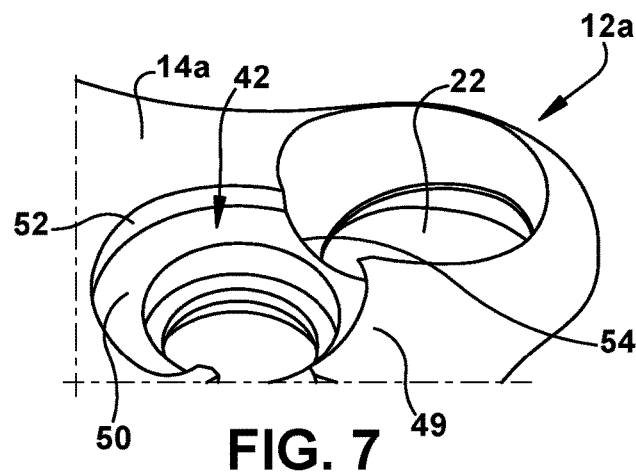
FIG. 7 is a partial perspective view of a top plate portion prior to full manufacturing and assembly of an expandable bone plate assembly according to an embodiment of the present disclosure.

The disclosure refers to the terms "top," "bottom," "front," and "back" with respect to certain components. These terms are used with respect to the orientation of an expandable bone plate assembly as illustrated in FIGS. 1 and 2. The disclosure also refers to the terms "left" and "right" with respect to certain components. These terms are used with respect to the orientation of an expandable bone plate assembly as illustrated in FIG. 1. The disclosure also refers to the term "lower" with respect to certain components. This term is used with respect to the orientation of a top plate portion as illustrated in FIG. 7. Further, as used herein with respect to a described element, the terms "a," "an," and "the" include at least one or more of the described element unless otherwise indicated. Further, the term "or" refers to "and/or" including combinations thereof unless otherwise indicated. In addition, the term "plurality" as used with respect to an element refers to more than one of the elements. In addition, it will be understood that when an element is referred to as being "over," "on," "attached" to, "connected" to, "coupled" to, "in fluid communication with," another element, it can be directly over, on, attached to, connected to, coupled to, in fluid communication with the other element or intervening elements may also be present. In contrast, when an element is referred to as being, for example, "directly over," "directly on," "directly attached" to, "directly connected" to, "directly coupled" to, or in direct fluid communication with another element, there are no intervening elements present. An element that is disposed "adjacent" another element may have portions that overlap or underlie the adjacent element. By "substantially" is meant that the shape, configuration, orientation or length of the element need not have the mathematically exact described shape, configuration, orientation or length but can have a shape, configuration, orientation or length that is recognizable by one skilled in the art as generally or approximately having the described shape, configuration, orientation or length.

Figure 3:
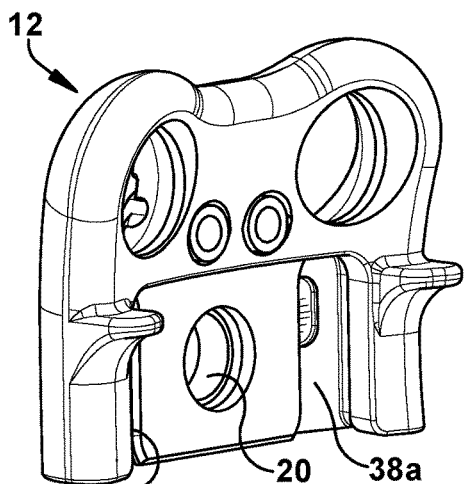
FIG. 3 is a side perspective view of a top plate portion of an expandable bone plate assembly according to an embodiment of the present disclosure.
Figure 18:
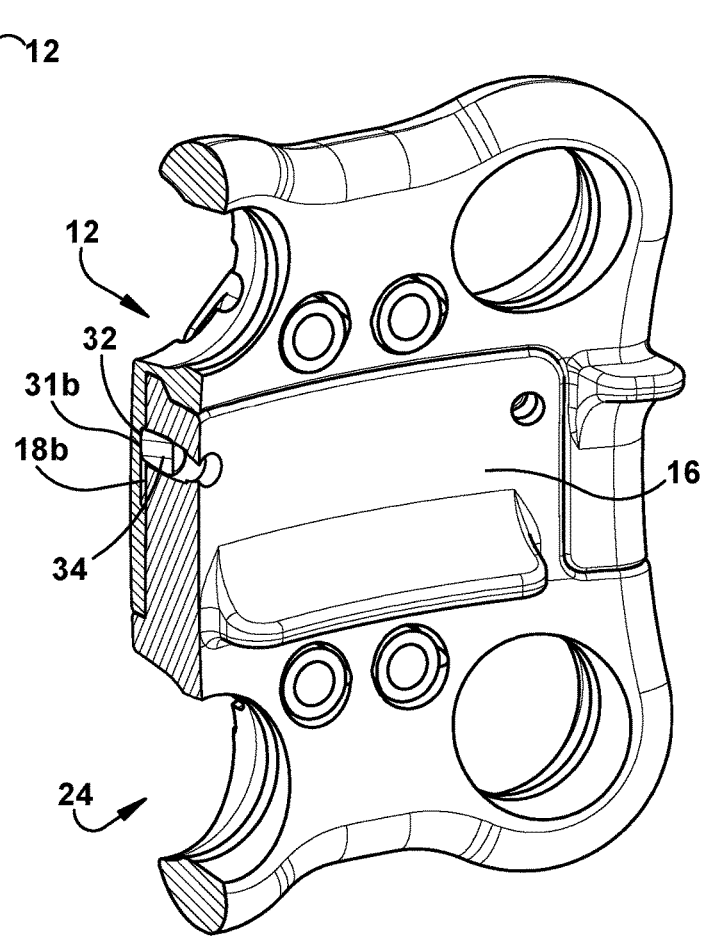
FIG. 18 is a partial cut-away view of an expandable bone plate assembly according to an embodiment of the present disclosure.

The present disclosure relates to expandable bone plate assemblies. Referring to FIGS. 1 and 2, in an embodiment, an expandable bone plate assembly 10 comprises a top plate portion 12 having a front side 14 and a back side 16. As illustrated in FIG. 18, back side 16 comprises a longitudinally extending blind slot 18. In certain embodiments, back side 16 comprises a left longitudinally extending blind slot and a right longitudinally extending blind slot. The length of longitudinally extending blind slot 18 determines the maximum height the expandable bone plate assembly can be expanded as described in more detail below. Top plate portion 12 also comprises a transversely extending counterbore 20 extending through the front and back sides 14 and 16 of the top plate portion 12. Transversely extending counterbore 20 does not necessarily extend at a right angle to the long axis Y of expandable bone plate assembly 10. Rather, transversely extending bore 20 extends along a plane different than the plane along which Y axis extends. Top plate portion 12 further includes a bone screw hole 22 extending through the front and back sides 14 and 16 of the top plate portion 12. Although the figures illustrate the top plate portion as having two bone screw holes, the top plate portion can have only one bone screw hole or a plurality of bone screw holes. In certain embodiments as illustrated in FIG. 3, the back side of top plate portion 12 comprises a longitudinally extending groove 38, such as a left longitudinally extending groove 38a and a right longitudinally extending groove 38b that is configured to accept a bottom plate portion of the plate assembly as described below.

Figure 5:
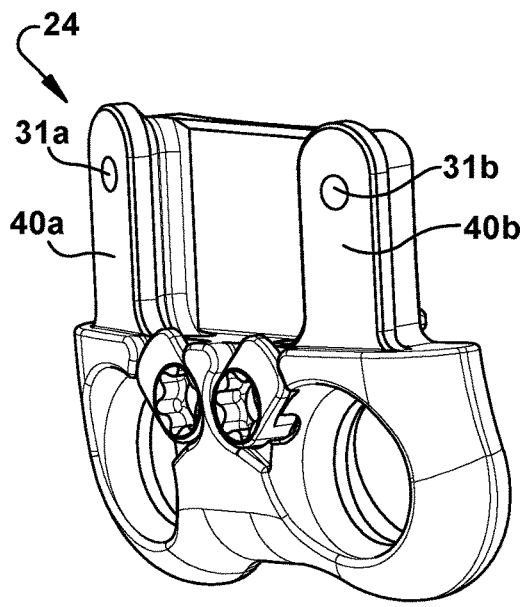
FIG. 5 is a perspective view of a bottom plate portion of an expandable bone plate assembly according to an embodiment of the present disclosure.

Expandable bone plate assembly 10 further comprises a bottom plate portion 24 comprising a front side 26, a back side 28, a transversely extending bore 30 extending through the front and back sides 26 and 28 of bottom plate portion 24 and a bone screw hole 32 extending through front and back sides 26 and 28 of bottom plate portion 24. The transversely extending bore can be a counterbore. The transversely extending bore does not necessarily extend at a right angle to the long axis Y of bone plate assembly 10. Rather, the transversely extending bore extends along a plane different than the plane along which Y axis extends. Although the figures illustrate two transversely extending bores in FIG. 6, a left transversely extending bore 30a and a right transversely extending bore 30b, the bottom plate portion can include only one transversely extending bore or a plurality of transversely extending bores. Similarly, although the figures illustrate the bottom plate portion as having two bone screw holes, the bottom plate portion can have only one bone screw hole or a plurality of bone screw holes. As illustrated in FIG. 5, the front side of the bottom plate portion can comprise a longitudinally extending tab 40, such as left longitudinally extending tab 40a and a right longitudinally extending tab 40b that is disposed in the respective left and right longitudinally extending grooves 38a and 38b of the back side of the top plate portion.

Figure 4:
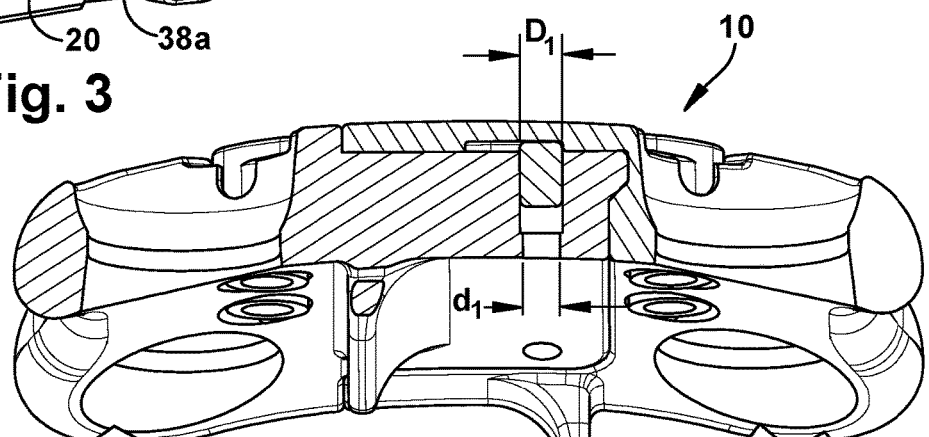
FIG. 4 is a side partial cross-sectional view of an expandable bone plate assembly according to an embodiment of the present disclosure.
Figure 6:
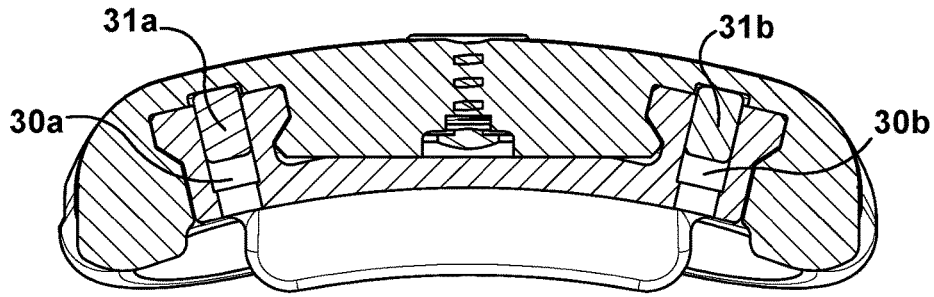
FIG. 6 is a side partial cross sectional view of an expandable bone plate assembly according to an embodiment of the present disclosure.

Referring to FIGS. 4, 6 and 18, bone plate assembly 10 further includes a pin 31 comprising a pin head 32 and a pin shaft 34 depending from pin head 32. Pin shaft 34 is disposed within transversely extending bore 30 of bottom plate portion 24 and has an outer diameter D1 greater than the minor diameter d1 of transversely extending bore 30. Pin head 32 is disposed against longitudinally extending blind slot 18 of top plate portion 12 as illustrated in FIG. 18. The number of pins in the bone plate assembly corresponds to the number of transversely extending bores of the bottom plate portion. Although the figures illustrate the expandable bone plate assembly as having a left pin 30a and a right pin 30b, the plate assembly can have only one pin or a plurality of pins. In embodiments where the transversely extending bore of the bottom plate portion is a counterbore, the pin head can comprise a flange that is disposed against the longitudinally extending blind slot of the top plate portion as described in detail in U.S. Patent Application No. 62/502,844 entitled: "Expandable Spinal Cage Assemblies for Supporting Bone Structures," filed on May 8, 2017, which is incorporated by reference in its entirety herein.

Bone plate assembly further comprises a lock screw 36 disposed within transversely extending counterbore 20 of top plate portion 12.

An advantage of such an expandable bone plate assembly is that the smaller components of the assembly such as the pin and lock screw are retained once the bone plate is assembled after manufacturing. This minimizes the risk of the expandable bone plate assembly coming apart after manufacturing (e.g. during shipping) and during and after implantation in a patient.

Figure 8:
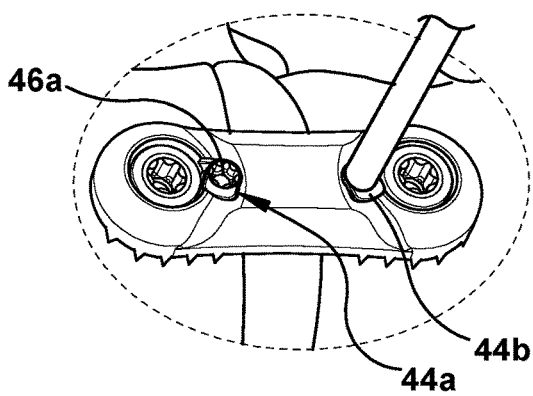
FIG. 8 is a perspective view illustrating bone screw locks being activated during a step of implanting an expandable bone plate assembly on vertebrae according to an embodiment of the present disclosure.
Figure 9:
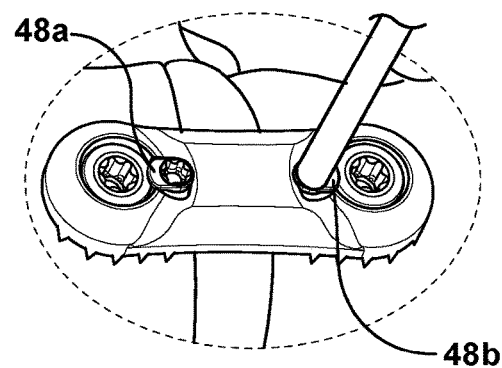
FIG. 9 is a perspective view illustrating bone screw locks being activated during a step of implanting an expandable bone plate assembly on vertebrae according to an embodiment of the present disclosure.

Bone plate assemblies can also include bone screw locks to prevent or minimize bone screws from backing out of the bone plate assemblies. For example, as illustrated in FIG. 7, a bone plate can comprise a recess 42 in fluid communication with a bone screw hole 22 of a top plate portion 12A. As shown in FIGS. 8 and 9, a rotatable bone screw lock 44 is mounted in the recess of top plate portion 12A and has a lock head 46 including a laterally extending flange 48, wherein in a locked position, a part of the laterally extending flange is within the bone screw hole of the top plate portion 45 as illustrated in FIG. 9.

Referring back to FIG. 7, recess 42 can be defined by a retention portion 49 of the front side 14A of top plate portion 12A, a lower surface 50 of top plate portion 12A, and a discontinuous wall 52 comprising a gap 54 in fluid communication with bone screw hole 22 of top plate portion 12A. In such an embodiment, the laterally extending flange of the bone screw lock has an outer edge that is below the front side of the top plate portion. In a locked position, a part of the laterally extending flange is within the gap 54 and another part of the lock head 46 is covered by retention portion 49 of top plate portion 12A. Such an embodiment of a bone screw lock is disclosed in U.S. Patent Application No. 62/474,768, entitled "Internal Fixation Device with Rotatable Screw Locks" filed on Mar. 22, 2017, which is incorporated by reference in its entirety herein. As illustrated in FIG. 1, the bone plate assembly can comprise a plurality of bone screw locks that correspond to the number of bone screw holes of the top plate portion and the bottom plate portion. Alternatively, a single bone screw lock can be used for more than one bone screw hole as illustrated and disclosed in U.S. Patent Application No. 62/474,768.

Figure 10A:
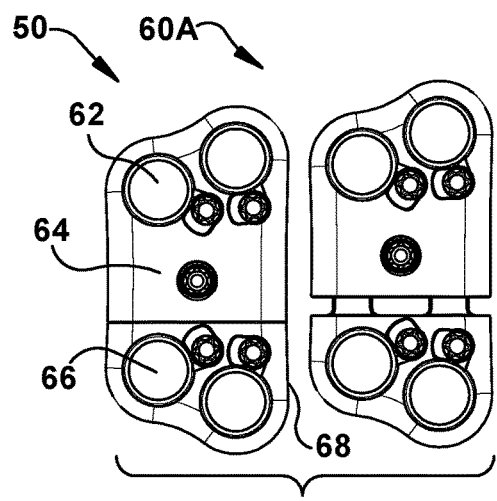
FIGS. 10A-10C are front views of a kit including expandable lateral bone plate assemblies according to an embodiment of a present invention illustrating such assemblies in a non-expanded position and a fully expanded position.
Figure 10B:
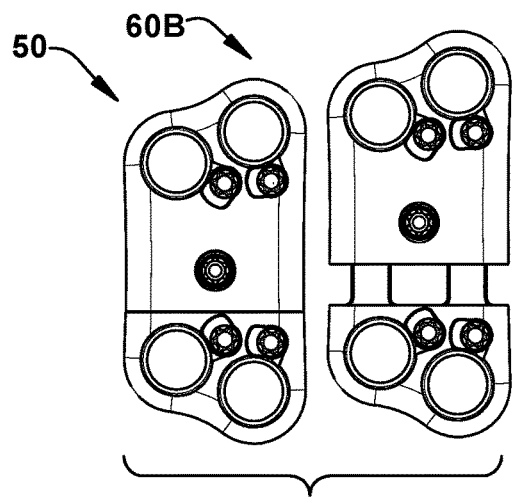
Figure 10C:
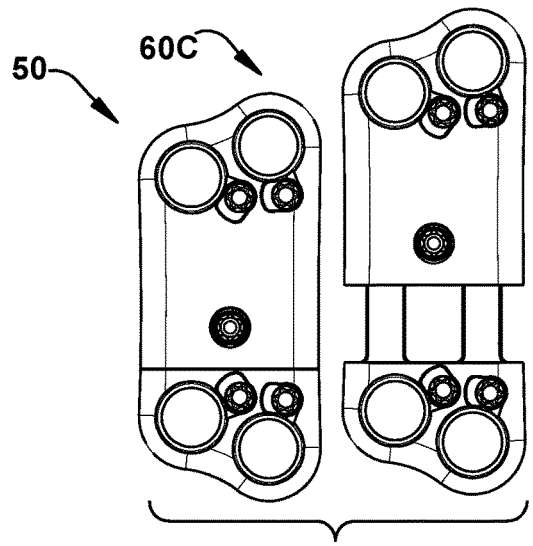
Figure 11:
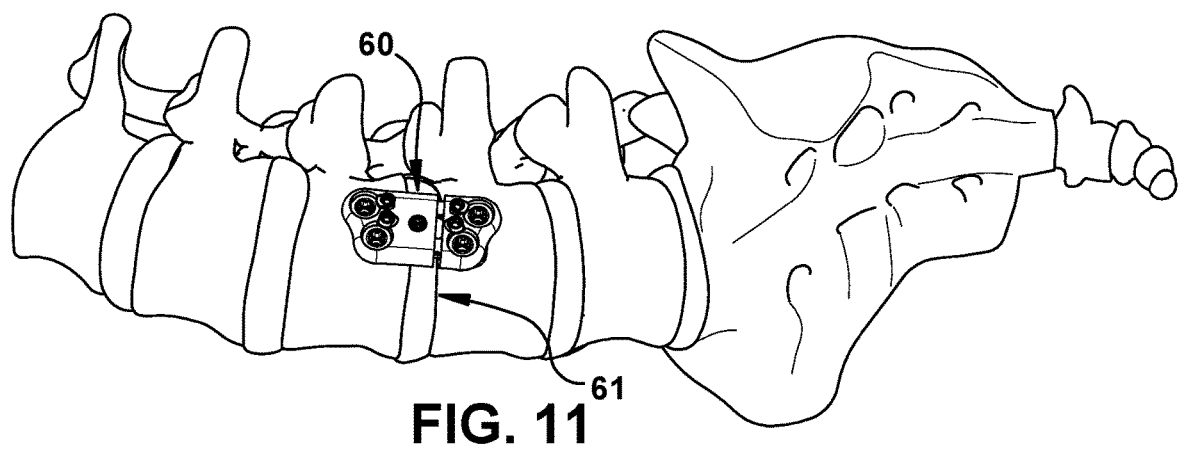
FIG. 11 is a perspective view of an expandable lateral bone plate assembly implanted on a lateral portion of vertebrae.

An expandable bone plate assembly can be part of a kit including expandable bone assemblies of different sizes. For example, kit 50 can include a plurality of expandable bone plate assemblies ranging in height in a fully expanded position. For example, referring to FIGS. 10A-10C, kit 50 can include three expandable lateral bone plate assemblies 60 ranging in size from approximately 25 millimeters (mm) to approximately 40 mm in a fully expanded position as measured from the center of the left screw hole 62 of top plate portion 64 to the center of left screw hole 66 of bottom plate portion 68. For example, expandable lateral bone plate assembly 60A schematically illustrated in FIG. 10A can range in height from approximately 22 mm in a non-expanded position to approximately 25 mm in a fully expanded position. Expandable lateral bone plate assembly 60B schematically depicted in FIG. 10B can range in height from approximately 25 mm in a non-expanded position to approximately 30 mm in a fully expanded position. Expandable lateral bone plate assembly 60C schematically illustrated in FIG. 10C can range in height from approximately 30 mm in a non-expanded position to approximately 44 mm in a fully expanded position. In certain embodiments, each expandable lateral bone plate assembly 60 includes four bone screw holes, four bone screw locks, is approximately 5 mm thick and is approximately 22 mm wide. Kit 50 can include different quantities of components of an expandable lateral bone plate assembly, different quantities of expandable lateral bone plate assemblies, and different configurations of expandable lateral bone plate assemblies so long as each expandable lateral bone plate assembly can stabilize adjacent bone structures. FIG. 11 illustrates an expandable lateral bone plate assembly 60 implanted on the lateral spinal region 61 in an expanded position.

Referring to FIGS. 12A-12C, kit 50 can additionally or alternatively include three expandable anterior lumbar bone plate assemblies 70 ranging in size from approximately 23 millimeters (mm) to approximately 35 mm in a fully expanded position as measured from the center of the left screw hole 72 of top plate portion 74 to the center of left screw hole 76 of bottom plate portion 78. For example, expandable anterior lumbar bone plate assembly 70A as schematically illustrated in FIG. 12A can range in height from approximately 21 mm in a non-expanded position to approximately 23 mm in a fully expanded position. Expandable anterior lumbar bone plate assembly 70B as schematically illustrated in FIG. 12B can range in height from approximately 23 mm in a non-expanded position to approximately 27 mm in a fully expanded position. Expandable anterior lumbar bone plate assembly 70C as schematically illustrated in FIG. 12C can range in height from approximately 27 mm in a non-expanded position to approximately 35 mm in a fully expanded position. In certain embodiments, each expandable anterior lumbar bone plate assembly 70 includes four bone screw holes, four bone screw locks, is approximately 5 mm thick and is approximately 28 mm wide. In certain embodiments, kit 50 includes plate portions having plate positioning flanges as described in more detail below. Kit 50 can include different quantities of components of an expandable anterior lumbar bone plate assembly, different quantities of expandable anterior lumbar bone plate assemblies, and different configurations of expandable anterior lumbar bone plate assemblies so long as each expandable anterior lumbar bone plate assembly can stabilize adjacent bone structures. FIG. 13 illustrates an expandable anterior lumbar bone plate assembly 70 implanted on the anterior lumbar spinal region 71 in an expanded position. Anterior lumbar bone plate assemblies can be used, for example, for L1-L5 vertebrae. Kit 50 can additionally or alternatively include expandable anterior sacrum bone plate assemblies that have similar configurations to expandable anterior lumbar bone plate assemblies. FIG. 14 illustrates an expandable anterior sacrum bone plate assembly 80 implanted on the anterior sacral spinal region 81 in an expanded position. Anterior sacrum bone plate assemblies can be used, for example, for L5-S1 vertebrae.

Any of the kits described above can include bone screws and installation tools.

Figure 15A:
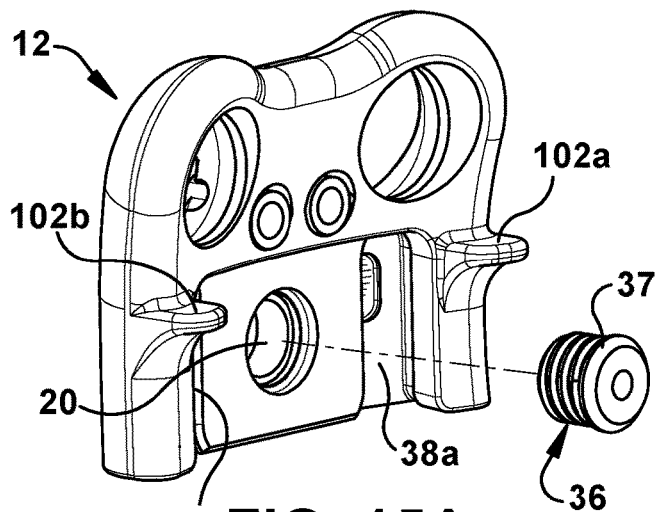
FIGS. 15A and 15B are perspective views of a top plate portion of an expandable bone plate assembly during one stage of manufacturing according to an embodiment of the present disclosure.
Figure 15B:
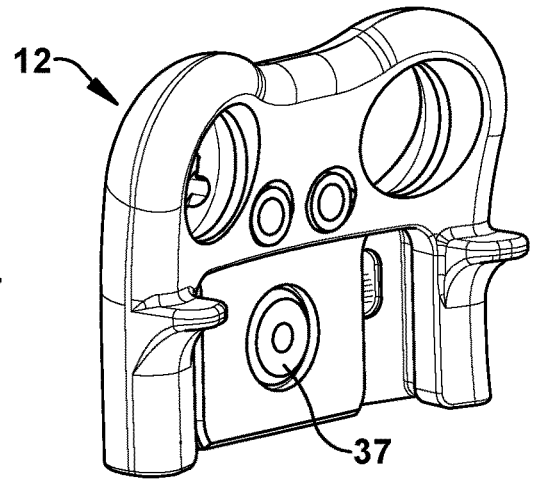
Figure 16A:
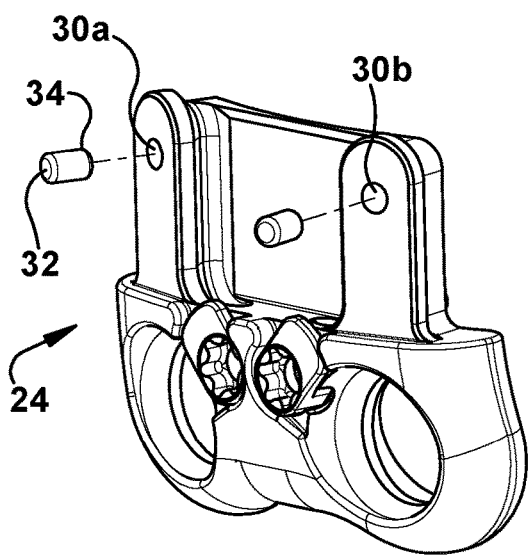
FIGS. 16A and 16B are perspective views of a bottom plate portion of an expandable bone plate assembly during another stage of manufacturing according to an embodiment of the present disclosure.
Figure 16B:
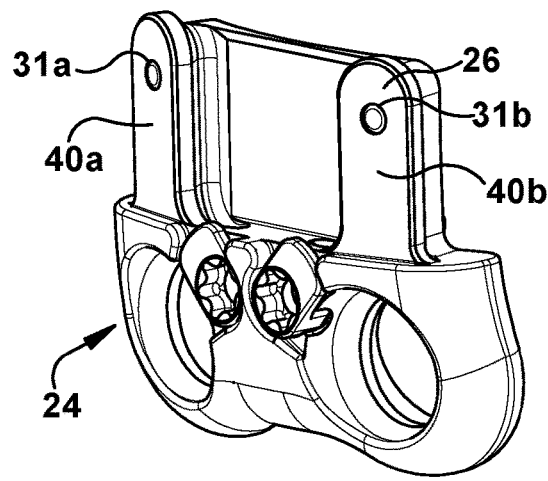
Figure 17:
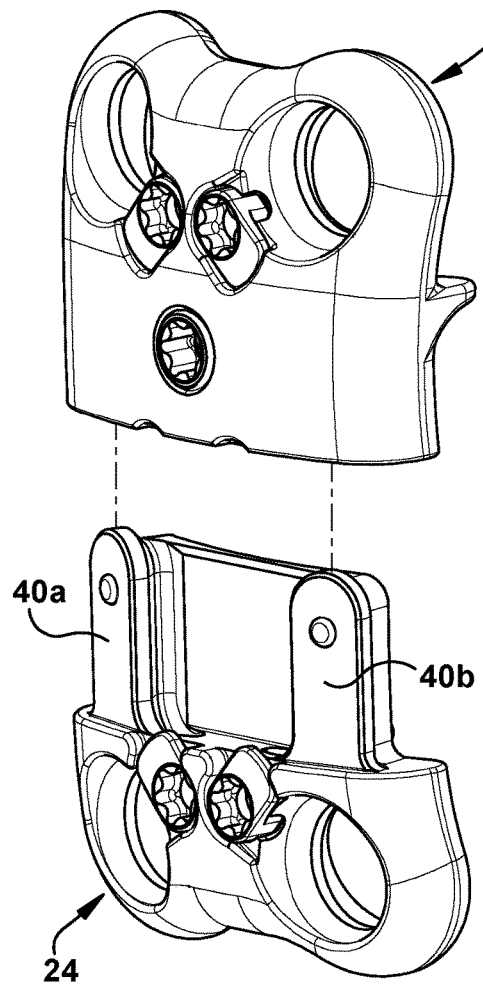
FIG. 17 is a perspective view of a top plate portion and a bottom plate portion of an expandable bone plate assembly during another stage of manufacturing according to an embodiment of the present disclosure.

FIGS. 15-17 illustrate different configurations of components of an expandable bone plate assembly at different stages of an exemplary manufacturing process. Referring to FIG. 15A, lock screw 36 is inserted into transversely extending counterbore 20 of top plate portion 12 until the lock screw head 37 bottoms on the counterbore's flat surface as schematically depicted in FIG. 15B. Referring to FIG. 16A, left pin 31a is inserted into left transversely extending bore 30a of bottom plate portion 24 and right pin 31b is inserted into right transversely extending bore 30b of bottom plate portion 24. The pins are inserted into the respective bores until the back of the pin shafts are flush with the immediately adjacent portions of front side 26 (such as longitudinally extending tabs 40a and 40b of bottom plate portion 24) as schematically illustrated in FIG. 16B. As indicated above, the outer diameter of the pin shaft is greater than the minor diameter of the transversely extending bore thereby creating an interference fit to retain the pin axially. Referring to FIG. 17, top plate portion 12 and bottom plate portion 24 are slide together. For example, left longitudinally extending tab 40a of bottom plate portion 24 can be inserted into left longitudinally extending groove 38a of top plate portion 12 and right longitudinally extending tab 40b of bottom plate portion 24 can be inserted into right longitudinally extending groove 38b of top plate portion 12. Referring to FIG. 18, the pins are pressed into their respective transversely extending bores until the pin heads 32 are bottomed into the longitudinally extending blind slots 18 of back side 16 of top plate portion 12. This prevent over-expansion of the bone plate assembly 10 as the bone plate portions can only be expanded the length of longitudinally extending blind slot 18 which does not extend through top and bottom ends of the back side of the top plate portion. FIG. 18 illustrates only right pin 31b bottomed into right longitudinally extending blind slot 18b for the sake of clarity but left pin 31a can similarly be bottomed into left longitudinally extending blind slot 18a. Pin 31b and optionally pin 31a retain expandable bone plate assembly 10 together so that the pins and lock screws are secured in the expandable bone plate assembly after manufacturing so that the components of the expandable bone plate assembly do not migrate out during transit (e.g. after manufacturing) and during and after implantation.

Figure 19:
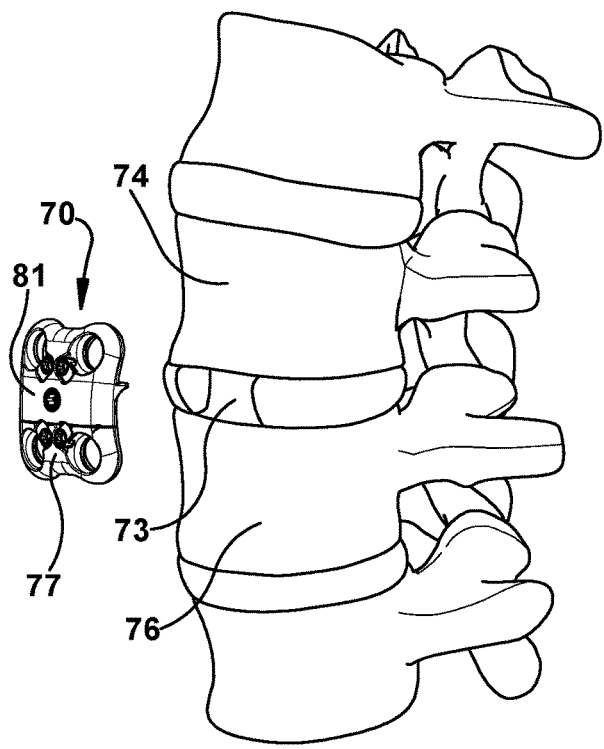
FIGS. 19 to 26 are perspective views illustrating an expandable bone plate assembly during various implantation steps during an anterior lumbar interbody fusion procedure according to an embodiment of the present disclosure.
Figure 20:
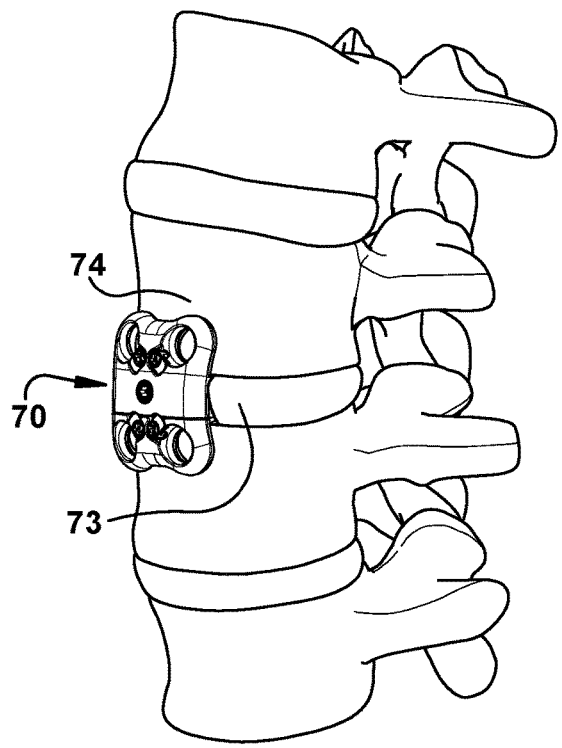
Figure 21:
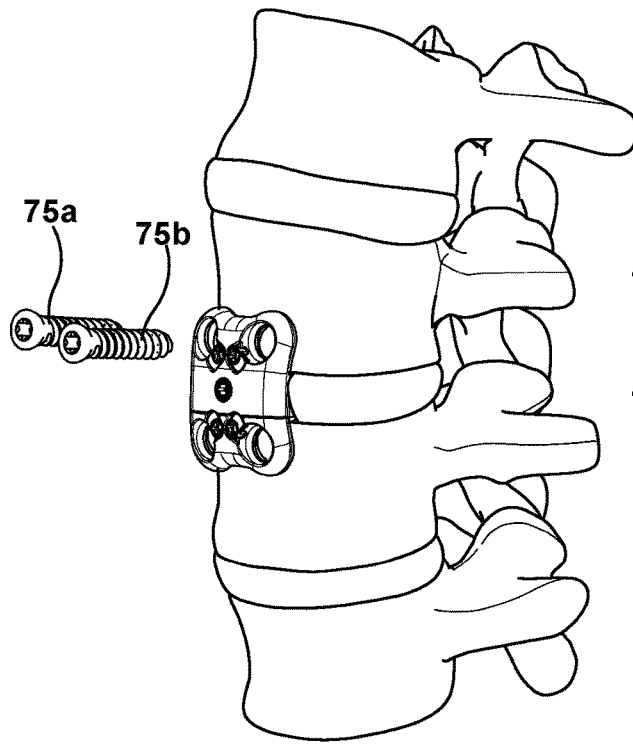
Figure 22:
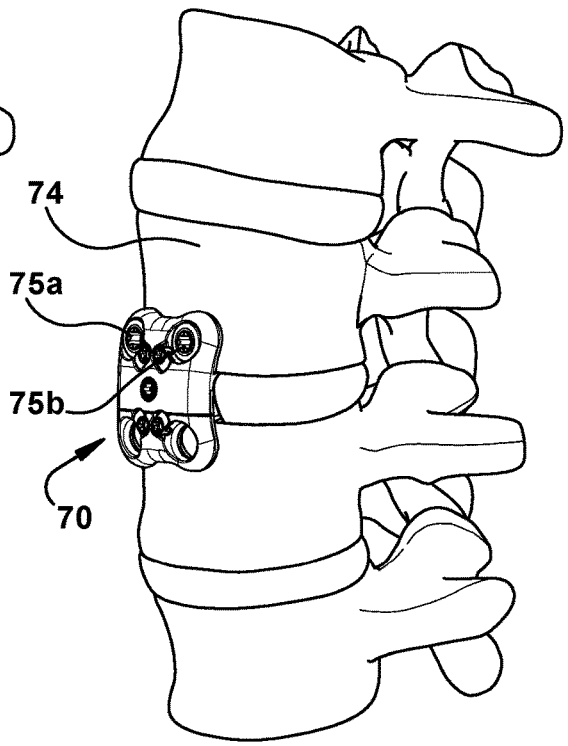
Figure 23:
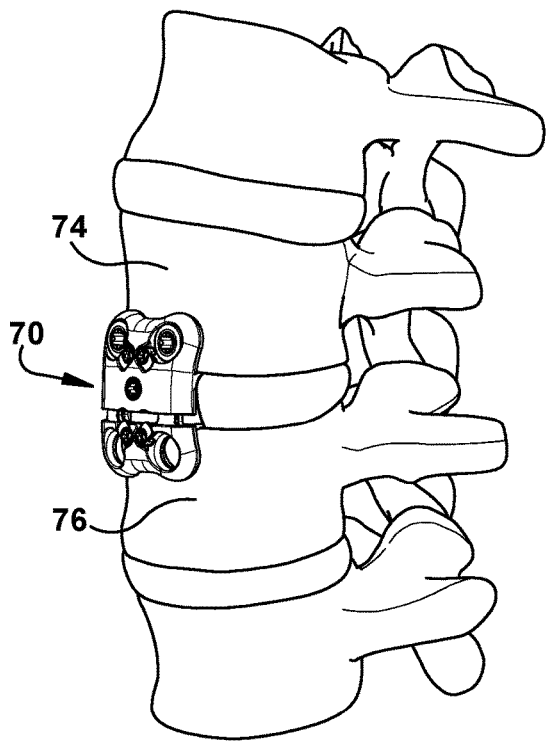
Figure 24:
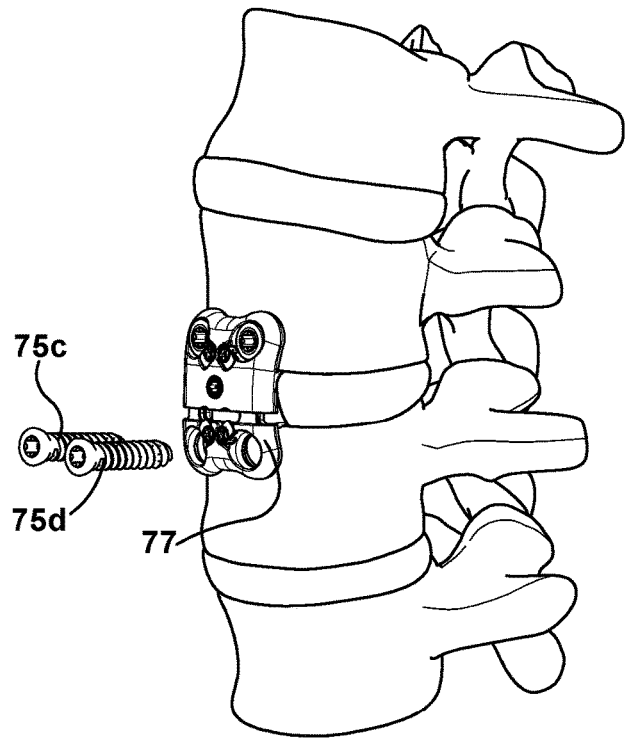
Figure 25:
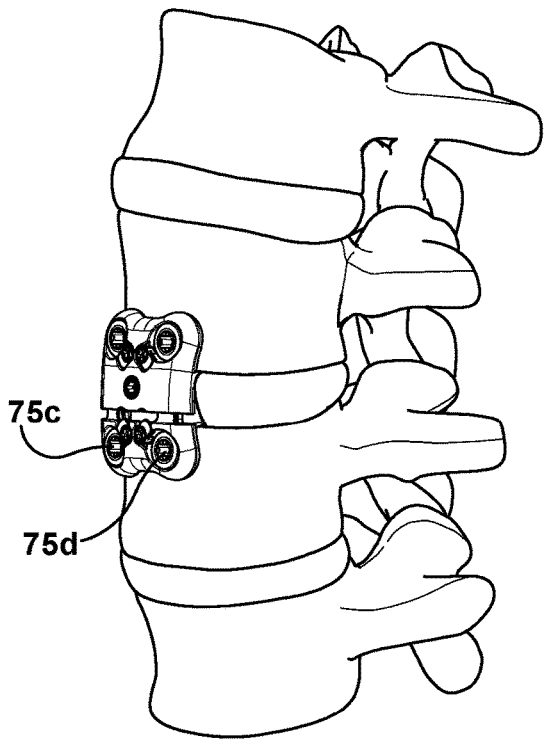
Figure 26:
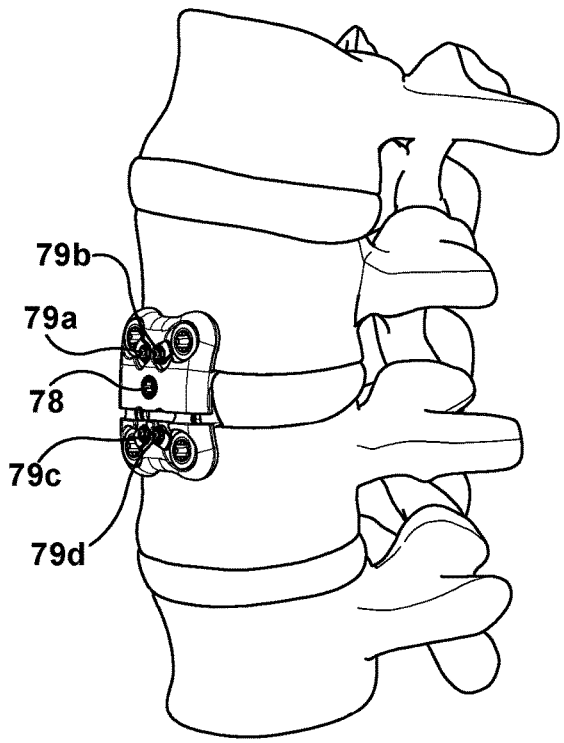

FIGS. 19 to 26 illustrate an exemplary method of implanting an expandable bone plate assembly for an anterior lumbar interbody fusion procedure. With reference to FIG. 19, a proper size of expandable plate assembly 70 selected to fit the prepared disk height. As illustrated in FIG. 20, bone plate assembly 70 is positioned in the disc space 73 while contacting the end plate 74 of one of the two adjacent vertebra. The proper bone screw type, size and length is selected to fit the patient's anatomy as depicted in FIG. 21. As illustrated in FIG. 22, the bone screws 75 are inserted into top plate portion 81 to retain the expandable bone plate assembly 70 to the vertebra 74 contacted in the second step described above as depicted in FIG. 20. The expandable bone plate assembly is expanded until contact is made with the opposite vertebra 76 as illustrated in FIG. 23. The proper bone screw type, size and length is selected to fit the patient anatomy as illustrated in FIG. 24. The remaining two bone screws 75 are inserted into the bottom plate portion 77 as shown in FIG. 25. Lock screw 78 is tightened to lock the expanded bone plate assembly into position and the four bone screw locks 79 are rotated to prevent migration of the bone screws 75 as depicted in FIG. 26.

Figure 27:
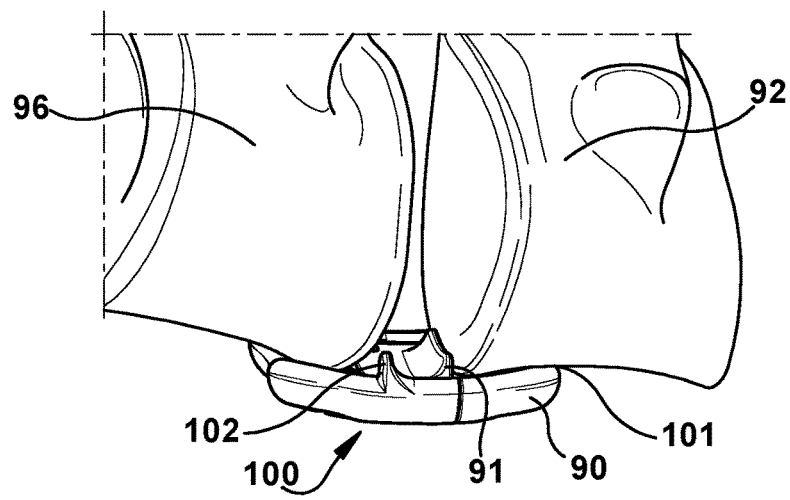
FIG. 27-32 are perspective views illustrating an expandable bone assembly with plate positioning flanges during various implantation steps on a proximal and distal vertebra according to an embodiment of the present disclosure.
Figure 28:
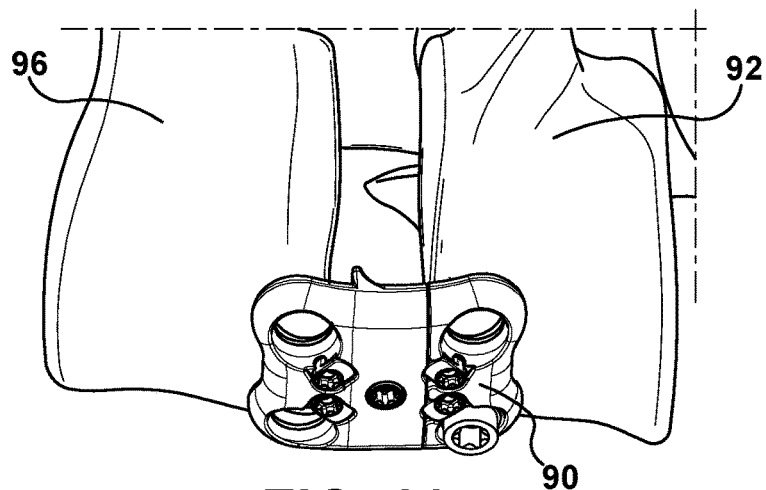
Figure 29:
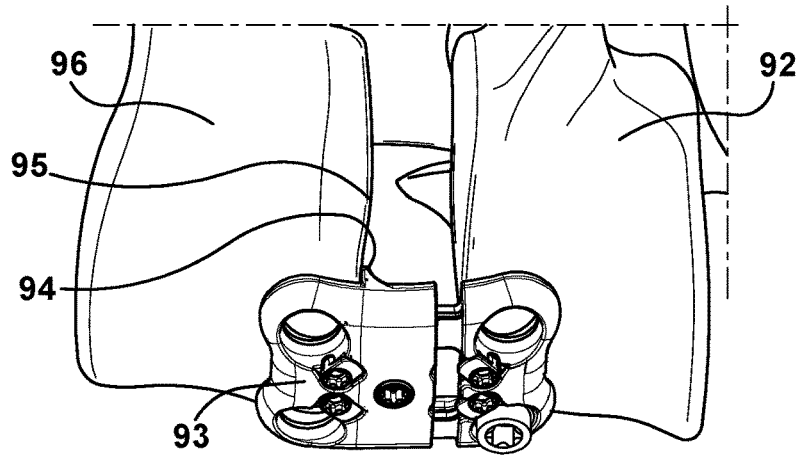
Figure 30:
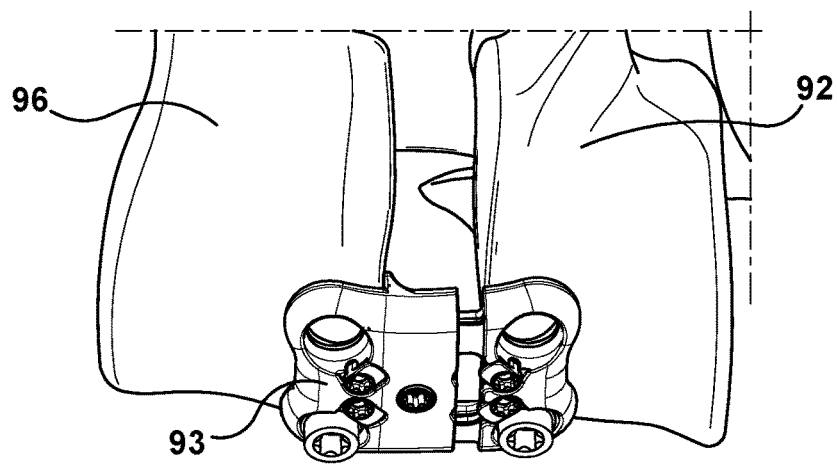
Figure 31:
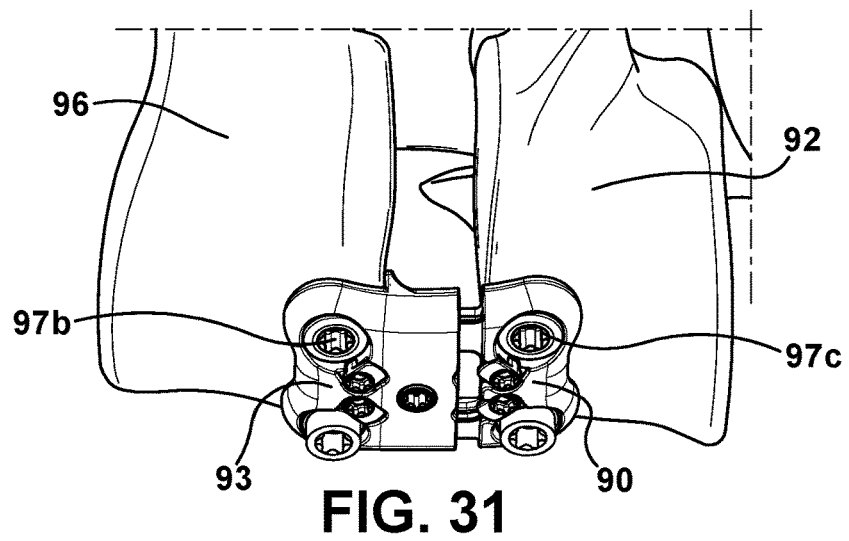
Figure 32:
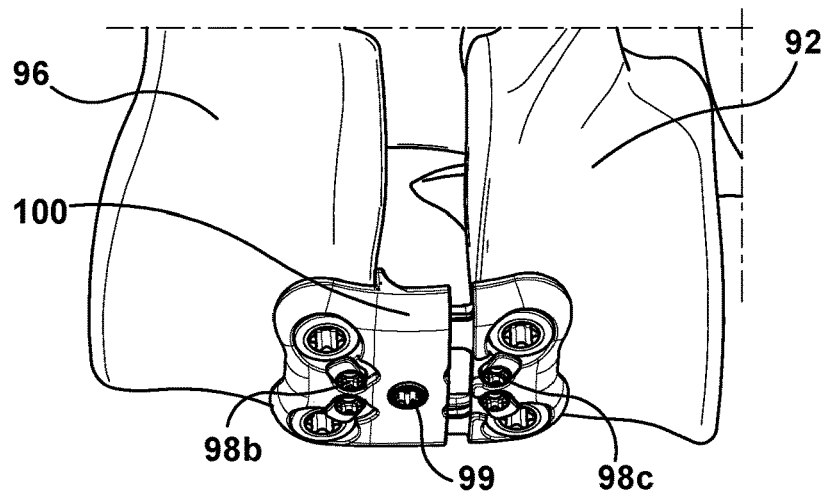

As stated above, in certain embodiments, a bone plate assembly includes positioning flanges extending from the back sides of top plate portion and the bottom plate portion of a bone plate assembly as depicted in FIGS. 2 and 3. With reference to FIG. 27 the positioning flange 91 of bottom plate portion 90 is positioned against the anterior rim 101 of the distal vertebral body 92. Bottom plate portion 90 is temporarily attached to distal vertebral body 92 as illustrated in FIG. 28. Referring to FIG. 29, top plate portion 93 is expanded until positioning flange 94 rests against the anterior rim 95 of the proximal vertebral body 96. Top plate portion 93 is temporarily attached to proximal vertebral body 96 as depicted in FIG. 30. Referring to FIG. 31, bone screws 97 are installed into top and bottom plate portions 93 and 90. Referring to FIG. 32, bone screw locks 98 are rotated to cover a portion of the bone screws 97 of top and bottom plate portions 93 and 90. The expandable bone plate assembly 100 is locked by applying torque (via a torque limiting handle, for example) to the lock screw 99 to tighten lock screw 99.

Figure 33:
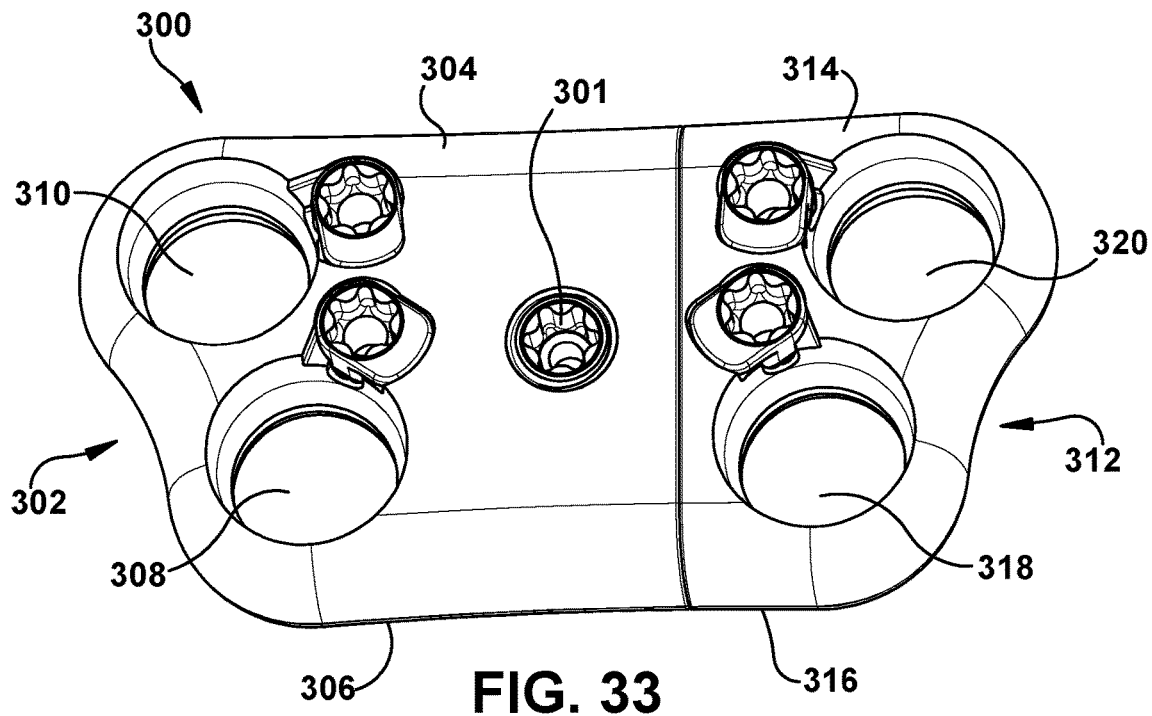
Figure 34:
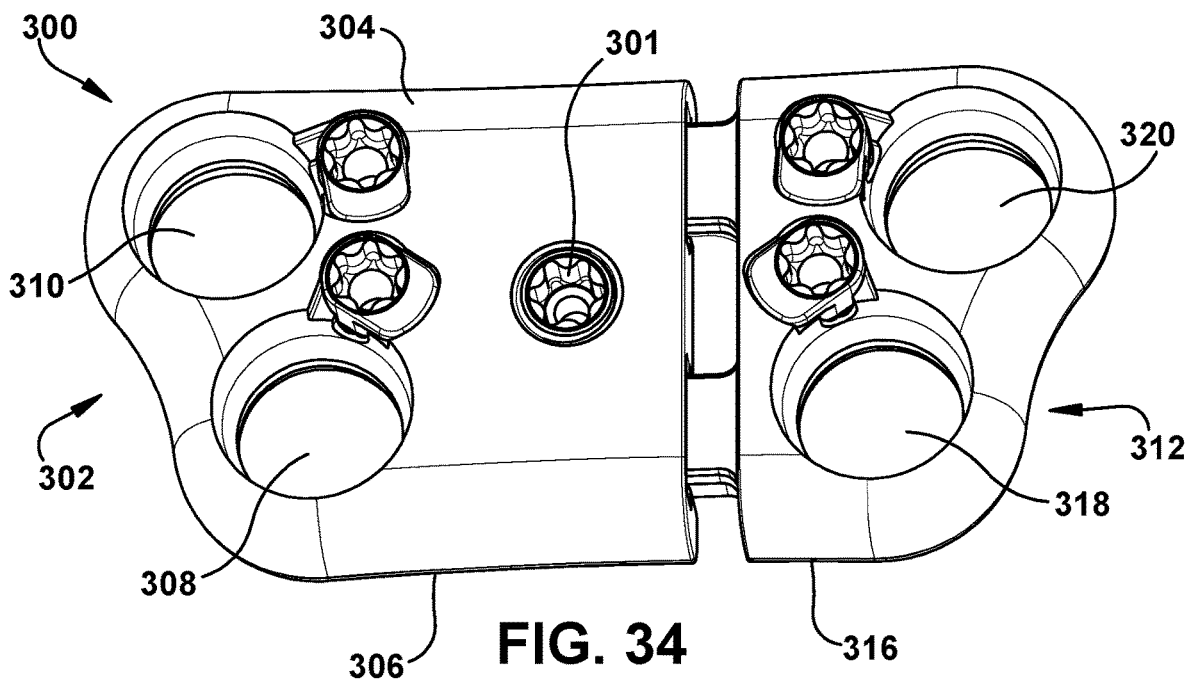

FIGS. 33-70 illustrate embodiments of expandable bone plate assemblies as well as steps of methods for implanting expandable bone plate assemblies. Although the methods are described and illustrated with respect to a lateral lumbar interbody fusion, the methods can be used for an anterior lumbar interbody fusion or other orthopedic procedures where an expandable bone plate assembly can be used. An exemplary expandable bone plate assembly 300 that can be used for such methods is illustrated in FIGS. 33 and 34. Expandable bone plate assembly 300 includes a first plate portion 302 comprising a front side 304, a back side 306, an anterior bone screw hole 308, and a posterior bone screw hole 310 both extending through the front and back sides 304 and 306 of first plate portion 302. Expandable bone plate assembly 300 also includes a second plate portion 312 slidably attached to first plate portion 302 and comprising a front side 314, a back side 316, an anterior bone screw hole 318, and a posterior bone screw hole 320 both extending through the front and back sides 304 and 306 of second plate portion 312. Expandable bone plate assembly 300 can also include a locking screw 301 that is mounted in a bore that extends through the front and back side of the first plate portion and contacts the front side of the second plate portion when tightened. The lock screw can be tightened to lock the bone plate assembly into a desired expanded configuration. FIG. 33 illustrates expandable bone plate assembly 300 in an expanded configuration and FIG. 34 illustrated expandable bone plate assembly 300 in an un-expanded configured. Expandable bone plate assembly 300 is only exemplary and can include other components including one or more of the components and features of expandable bone plate assemblies described above. Likewise, bone plates other than those described herein can be used including fixed bone plates where the length of the bone plate is not adjustable.

Figure 35:
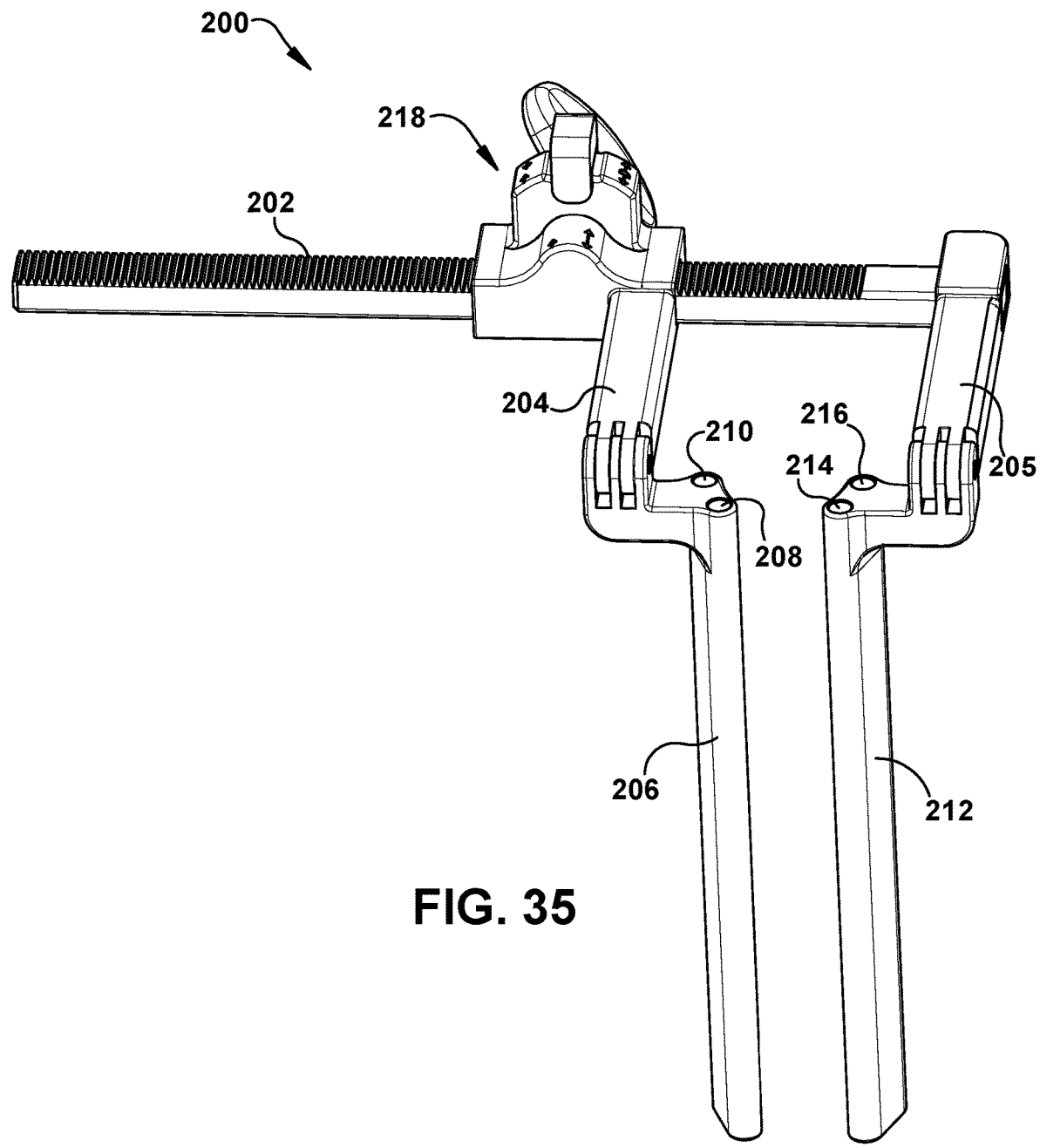

A method of implanting an expandable bone plate assembly can utilize a device that serves as both a distraction and compression instrument. An exemplary instrument is illustrated in FIG. 35. In particular, an exemplary orthopedic instrument 200 for adjusting a space between adjacent vertebrae comprises a ridged shaft 202, a first arm 204 slidably attached to the ridged shaft 202 and a second arm 205 attached to ridged shaft 202. Second arm 205 is illustrated as being fixedly attached to ridged shaft 202 but can be slidably attached to ridged shaft 202 as well. Orthopedic instrument 200 further includes a first guide 206 depending from first arm 204. First guide 206 comprises an anterior cannula 208 axially alignable with anterior bone screw hole 308 of first plate portion 302 and a posterior cannula 210 axially alignable with posterior bone screw hole 310 of first plate portion 302. In other words, the axis of anterior cannula 208 can be aligned with the axis of anterior bone screw hole 308 of first plate portion 302 and the axis of posterior cannula 210 can be aligned with the axis of posterior bone screw hole 310 of first plate portion 302. Orthopedic instrument 200 also includes a second guide 212 depending from second arm 205 and comprising an anterior cannula 214 axially alignable with anterior bone screw hole 318 of second plate portion 312 and a posterior cannula 216 axially alignable with posterior bone screw hole 320 of second plate portion 312. In other words, the axis of anterior cannula 214 can be aligned with the axis of anterior bone screw hole 318 of second plate portion 312 and the axis of posterior cannula 216 can be aligned with the axis of posterior bone screw hole 320 of second plate portion 312. Orthopedic instrument 200 also includes a control device 218 operably connected to ridged shaft 202 and first arm 204 for adjusting the position of first arm 204 along ridged shaft 202.

Figure 36:
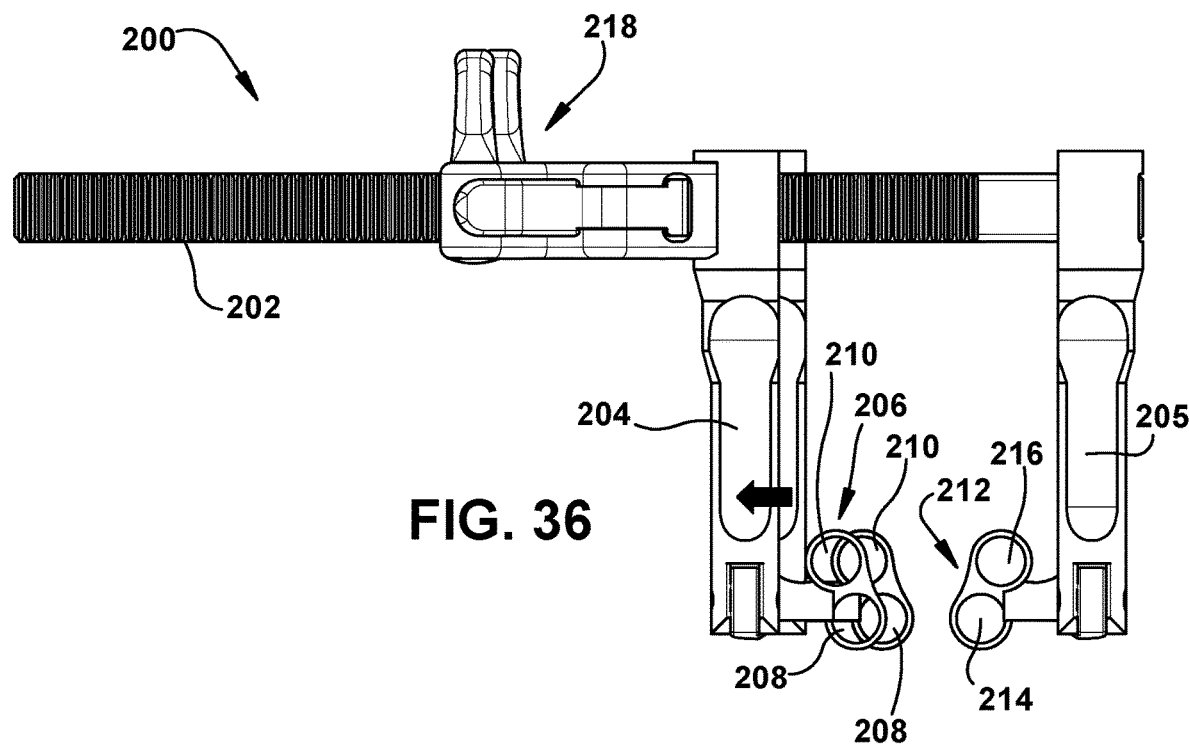
Figure 37:
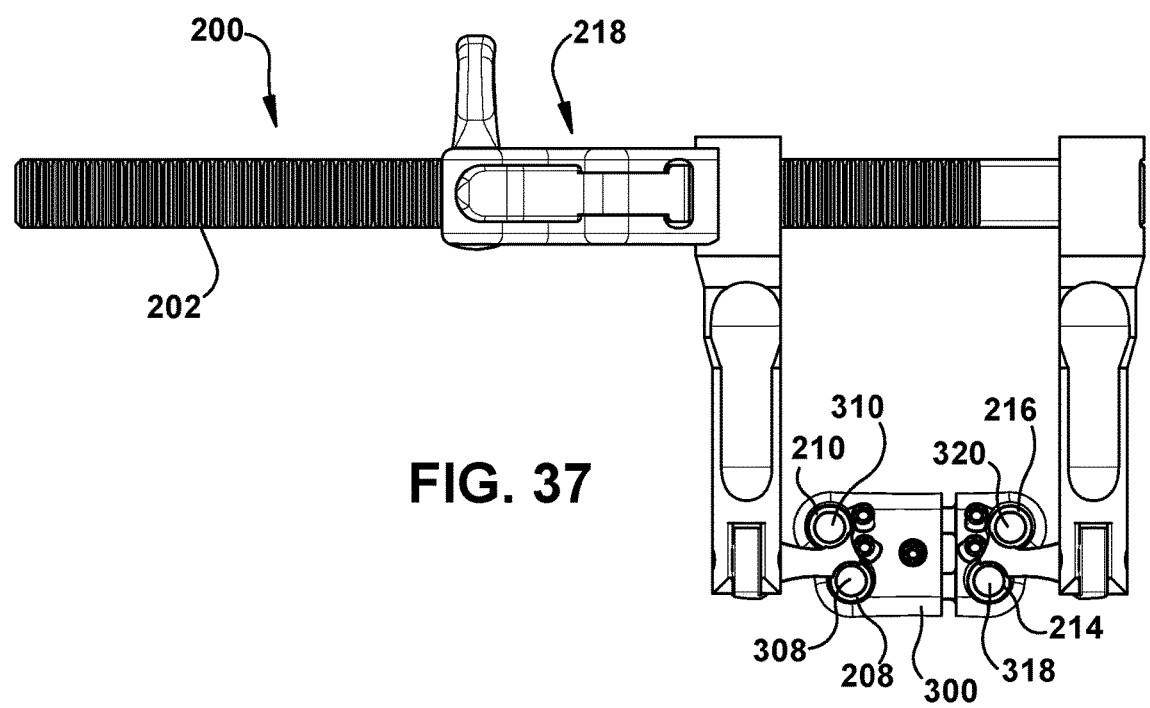

FIG. 37 illustrates anterior and posterior cannulas 208, 210, 214, and 216 of orthopedic instrument 200 axially aligned with anterior and posterior screw holes 308, 310, 318, and 320 of first and second plate portions 302 and 312 of expandable bone plate assembly 300. FIG. 36 illustrates orthopedic instrument 200 in two different positions. The distance between first and second guides 206 and 212 of orthopedic instrument 200 is adjustable via control device 218. However, the distance between the anterior and posterior cannulas of each guide is fixed. As such, the expandable bone plate assembly can be expanded to fit the distance between the first and second guides. In embodiments of a kit including expandable bone plate assemblies of different sizes, the distance between the first and second guides can dictate which of the expandable plates is used.

As illustrated in FIGS. 38 and 39, in an exemplary method, a guide pin 400 (which can also serve as a distractor/compressor pin) can be inserted at a desired location of vertebrae 402. For example, an anterior guide pin 400a can be inserted into an anterior location of vertebrae 402 using a pin inserter 500 (illustrated in FIG. 41a). Anterior cannula 214 of second guide 212 of second arm 205 of orthopedic instrument 200 can be slide over anterior guide pin 400a as depicted in FIG. 40. Control device 218, which is illustrated in FIG. 40 as being a thumbwheel, can adjust the distance between first and second arms 204 and 205 to expand orthopedic instrument 200 to set the location of remaining guide pins 400.

Referring to FIG. 41a, pin inserter 500 can be used to insert anterior guide pin 400b through anterior cannula 208 of first guide 206 into an anterior location of vertebrae 404. As seen in FIG. 41b, the depth a guide pin is inserted into bone can be determined by measurement markers on shaft 502 of pin inserter 500.

Figure 43:
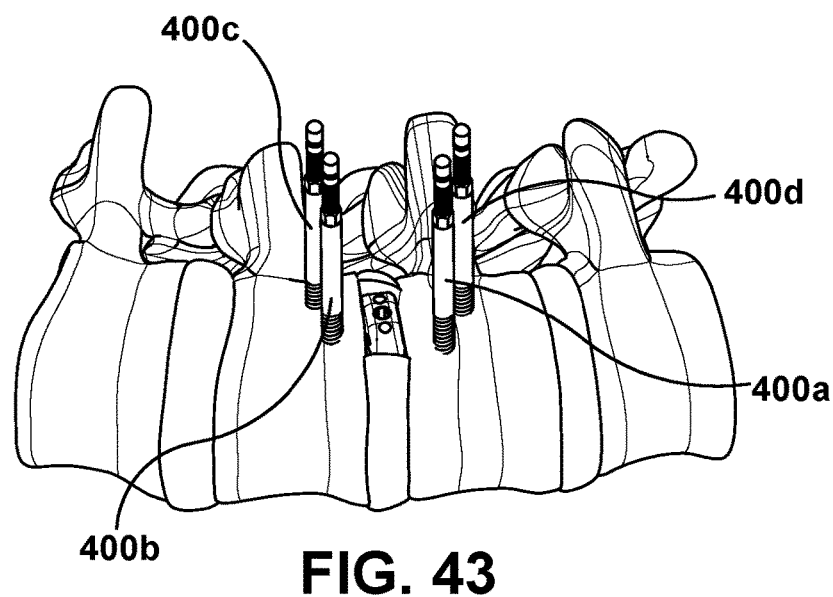

Referring to FIG. 42a, orthopedic instrument 200 can be used to distract the disc space between vertebrae 402 and 404 by using the control device 218 to slide first arm 204 away from second arm 205 for example. After distraction, an interbody device 600, illustrated in FIG. 42b can be inserted into the distracted disc space 602. To induce lordosis, disc space 602 can be distracted before installing posterior pin 400c through posterior cannula 210 of first arm 204 into a posterior location of vertebrae 404 and posterior pin 400d through posterior cannula 216 of second arm 205 into a posterior location of vertebrae 402. After disc space 602 has been distracted, tension can be released from orthopedic instrument 200 and it can be removed from the surgical working field leaving pins 400 installed in vertebrae 402 and 404 as seen in FIG. 43.

Figure 44:
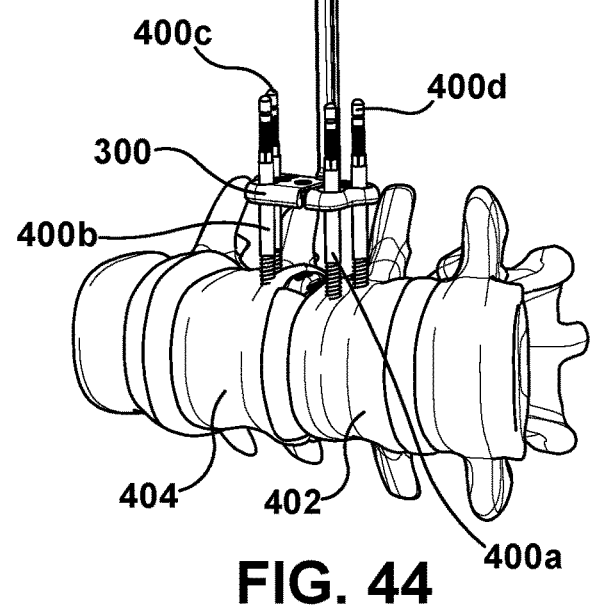
Figure 45:
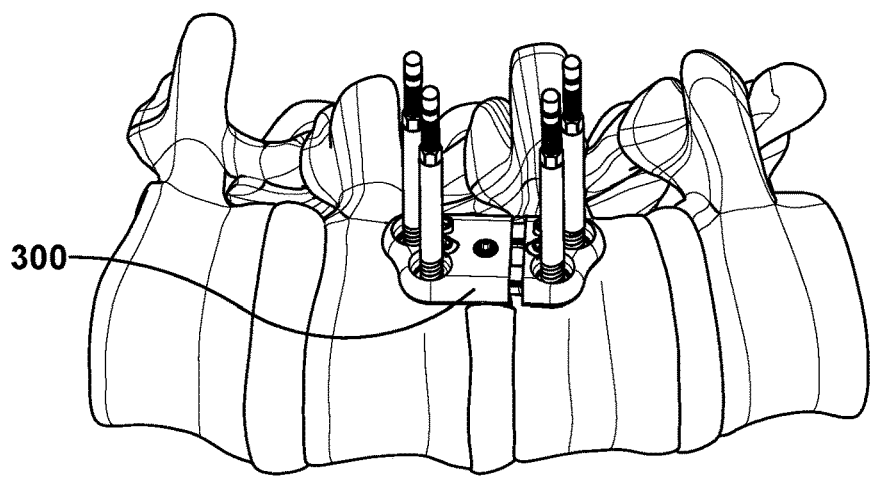
Figure 46:
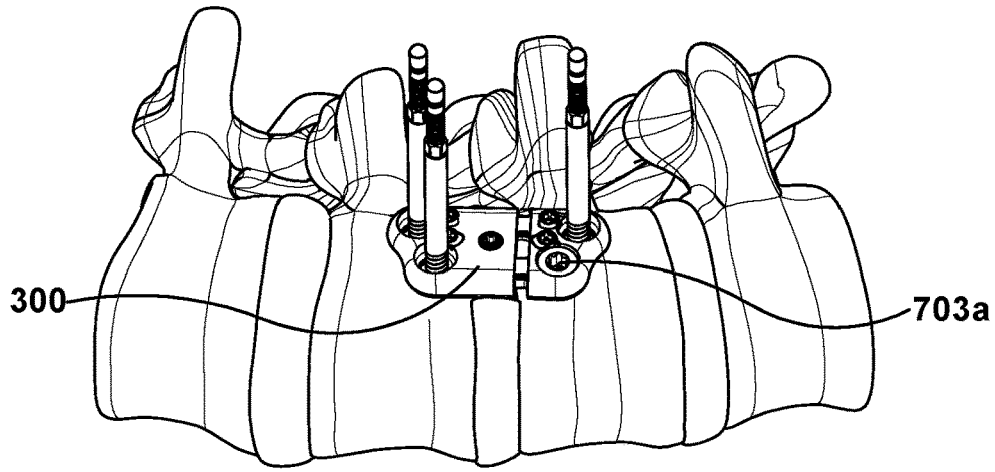
Figure 47:
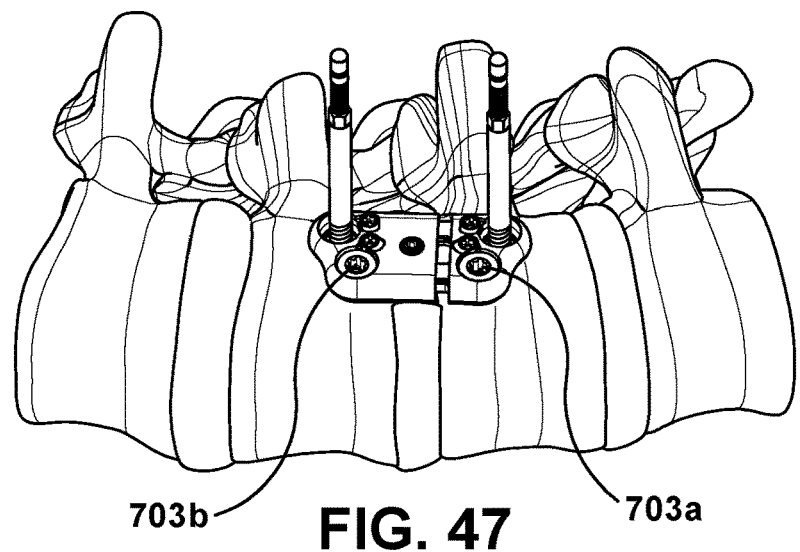

As shown in FIG. 44, a plate inserter 700 can be releasably coupled to expandable plate assembly 300 and can be used to slide expandable plate assembly 300 over pins 400 to place expandable plate assembly 300 against vertebrae 402 and 404 as illustrated in FIG. 45. The two anterior pins 400a and 400b can be removed and anterior bone screw 703a can be fully seated into anterior bone screw hole 318 of second plate portion 312 and anterior bone screw 703b can be fully seated into anterior bone screw hole 308 of first plate portion 302 as illustrated in FIGS. 46 and 47. Advantageously, the holes in vertebrae 402 and 404 created by distraction pins 400 can serve as pilot holes for insertion of bone screws 703. Further drilling or tapping of the pilot holes may be required depending on the hardness of vertebrae 402 and 404.

Figure 48:
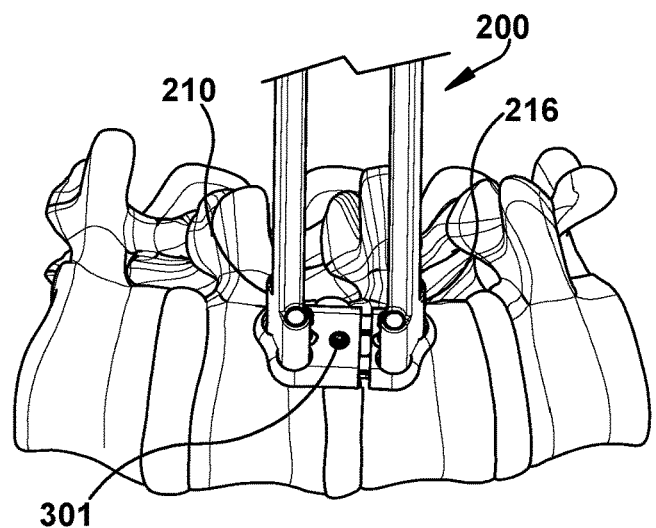
Figure 49:
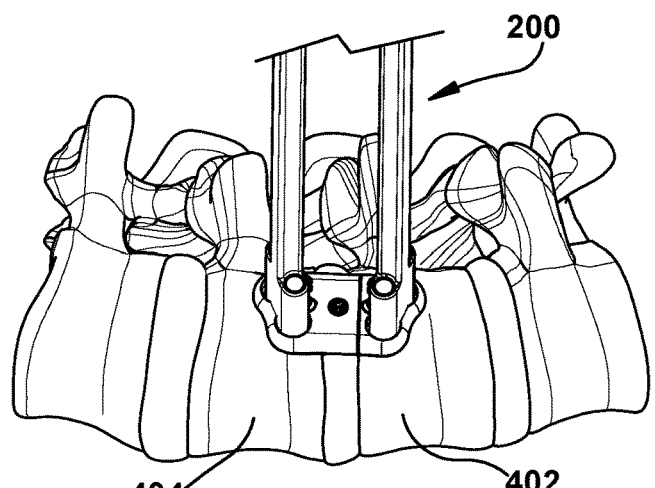
Figure 50:
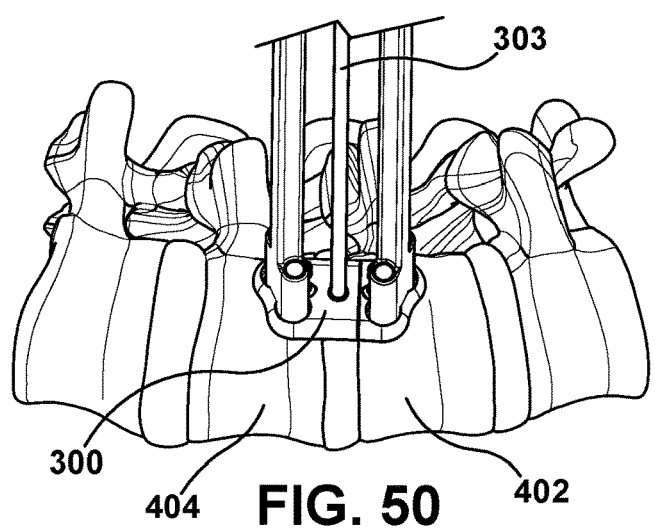

Referring to FIG. 48, disc space 602 optionally can be compressed. To do so, orthopedic instrument 200 is slide over the posterior guide pins 400c and 400d. In particular, posterior cannula 210 of first arm 204 is slide over posterior pin 400c and posterior cannula 216 of second arm 205 is slide over posterior pin 400d. Orthopedic instrument is then adjusted to compress disc space 602 as depicted in FIG. 49 by using the control device 218 to slide first arm 204 towards from second arm 205 for example. As compression force is being applied to vertebrae 402 and 404, locking screw 301 of bone plate assembly can be tightened with a driver 303, as depicted in FIG. 50, thereby preserving and maintain the compression load applied to vertebrae 402 and 404. In particular, the tightened lock screw 301 preserves the compression of the disc space after the compression force applied by orthopedic instrument 200 is removed.

Figure 51:
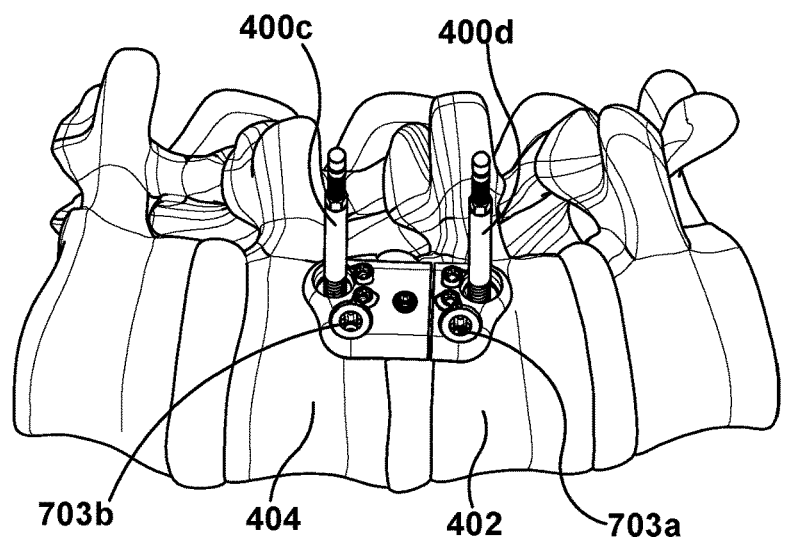
Figure 52:
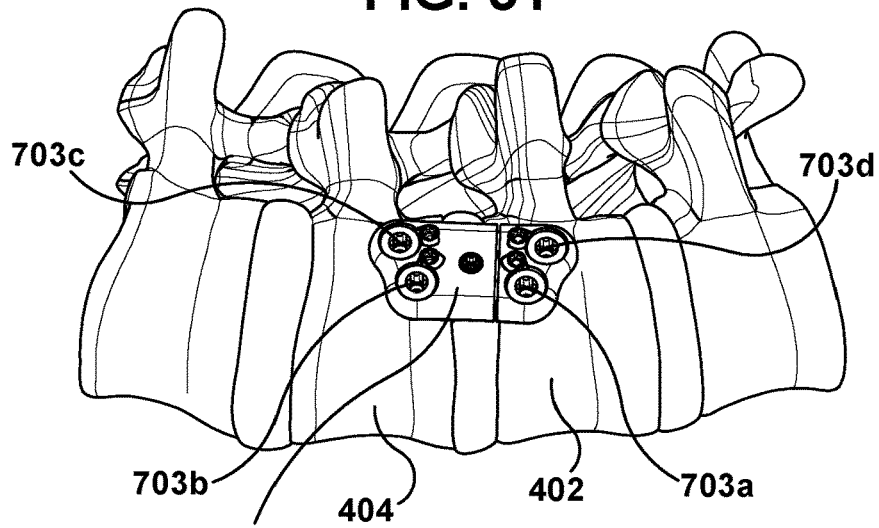
Figure 53:
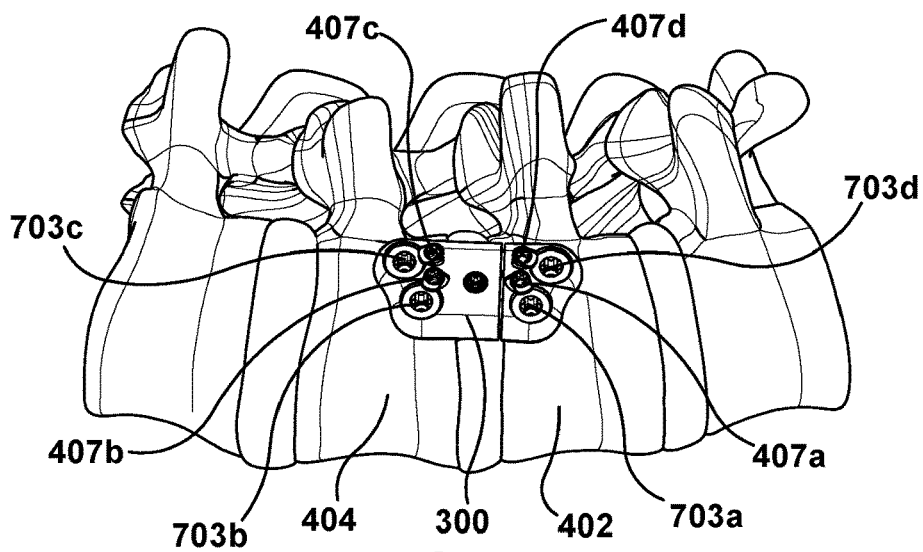

Referring to FIG. 51, after the compression force applied by orthopedic instrument 200 is released, orthopedic instrument 200 is removed. Posterior guide pins 400c and 400d are removed and bone screws 703c and 703d are inserted into the holes created by posterior distractor pins 400c and 400d as illustrated in FIG. 52. Referring to FIG. 53, in embodiments of an expandable bone plate assembly including bone screw locks, the bone screw locks 407 are rotated over the respective bone screws 703 as depicted in FIG. 53. The same instrument used to tightened lock screw 301 can be used to rotate bone screw locks 407 over bone screws 703.

Figure 54:
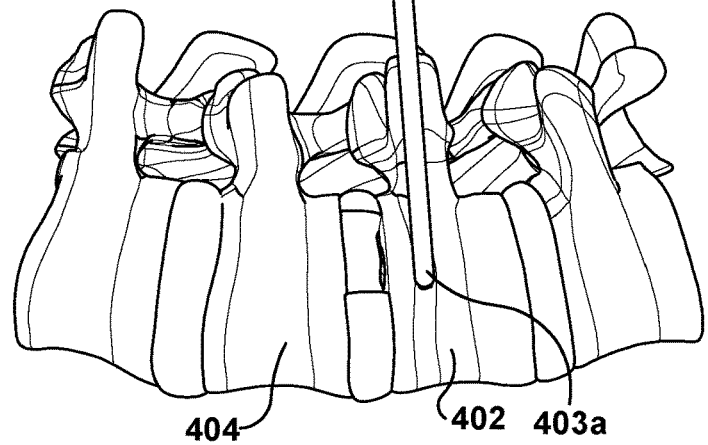
Figure 55:
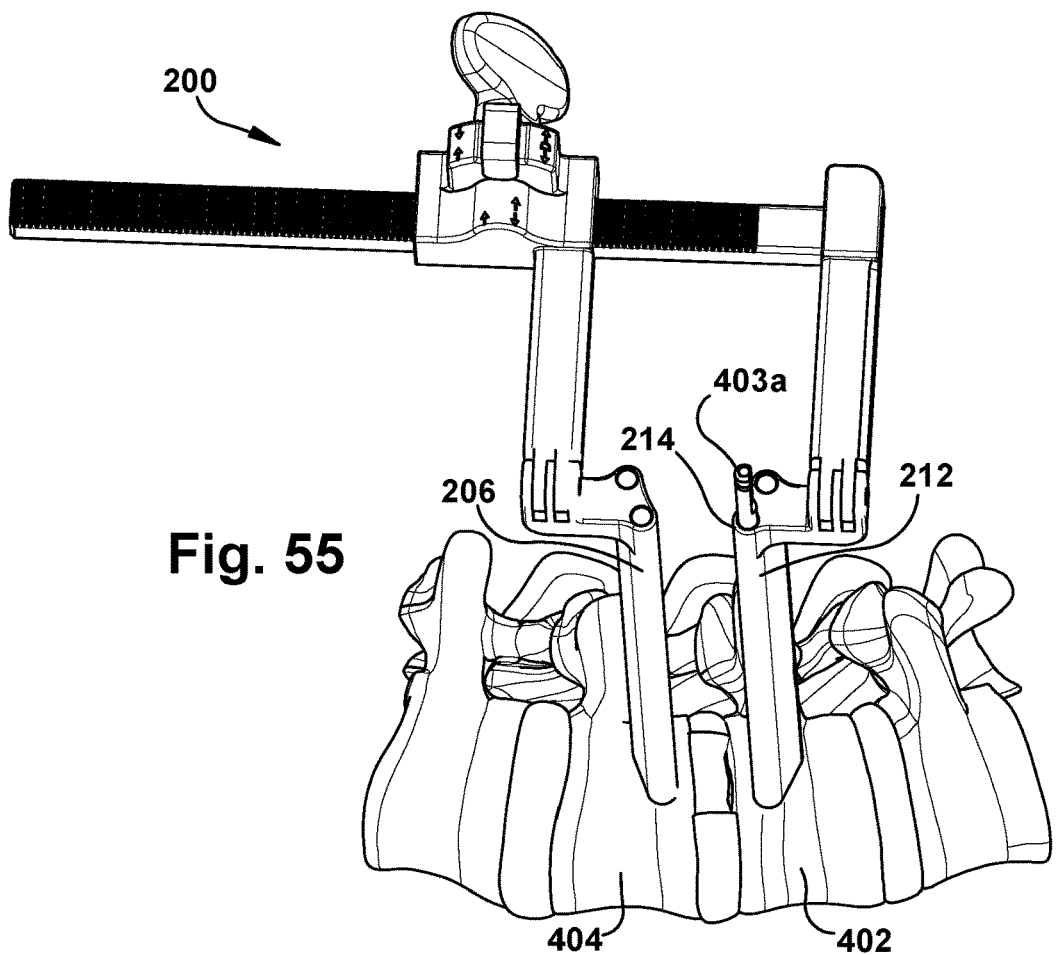

FIGS. 54-64 illustrate steps of another embodiment of a method of implanting an expandable bone plate assembly and devices used therefor. Referring to FIG. 54, a pin inserter 500 can be used to insert a guide pin 403 at a desired location of a vertebra, such as vertebra 402. Orthopedic instrument 200 is aligned with guide pin 403 and cannula 214 of orthopedic instrument 200 is slide over pin 403a until the distal end of orthopedic instrument 200 contacts vertebrae 402 and 404 as illustrated in FIG. 55. Although FIGS. 54 and 55 illustrate an anterior guide pin 403a inserted into vertebrae 402 and disposed within anterior cannula 214 of second guide 212, another guide pin could be inserted at a different location of a different vertebrae.

Using orthopedic instrument 200 as a guide, the remaining guide pins 403 are inserted through the respective cannulas of orthopedic instrument 200 as shown in FIG. 56. The depth the guide pins are inserted are marked on the ends of the guide pins that exit the cannulas of the orthopedic instrument. Disc space 602 between vertebrae 402 and vertebrae 404 can be distracted by using control device 218 to slide first arm 204 away from second arm 205, for example. Interbody device 600, illustrated in FIG. 57, then can be inserted into disc space 602.

Figure 59:
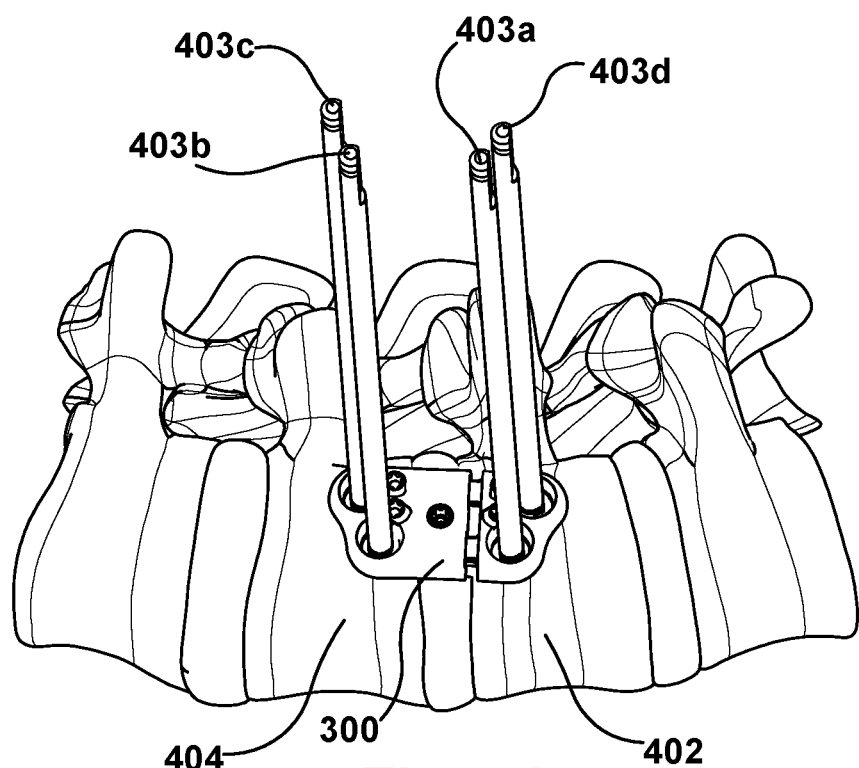

Tension can be released from orthopedic instrument 200 and it can be removed from the surgical working field. As shown in FIG. 58, expandable bone plate assembly 300 can be slide over guide pins 403 and can fall into place onto vertebrae 402 and 404 following the guidance of the four guide pins 403 as shown in FIG. 59.

Figure 60:
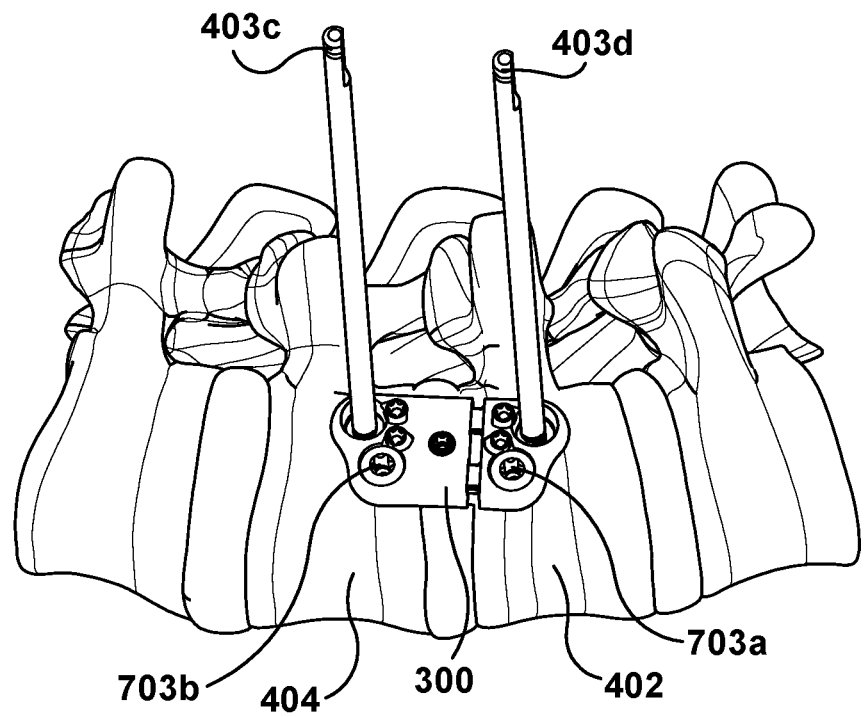

Referring to FIG. 60, the two anterior guide pins can be removed and anterior bone screws 703a and 703b can be fully seated against expandable bone plate assembly 300. Advantageously, the holes in vertebrae 402 and 404 created by guide pins 403 can serve as pilot holes for insertion of bone screws 703. Further drilling or tapping of the pilot holes may be required depending on the hardness of vertebrae 402 and 404.

Figure 61:
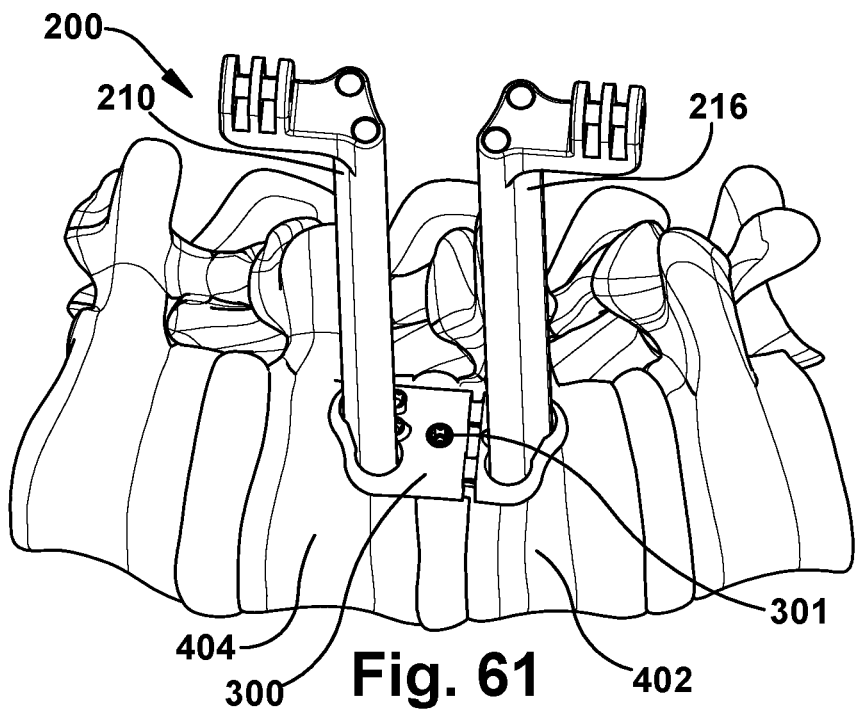
Figure 62:
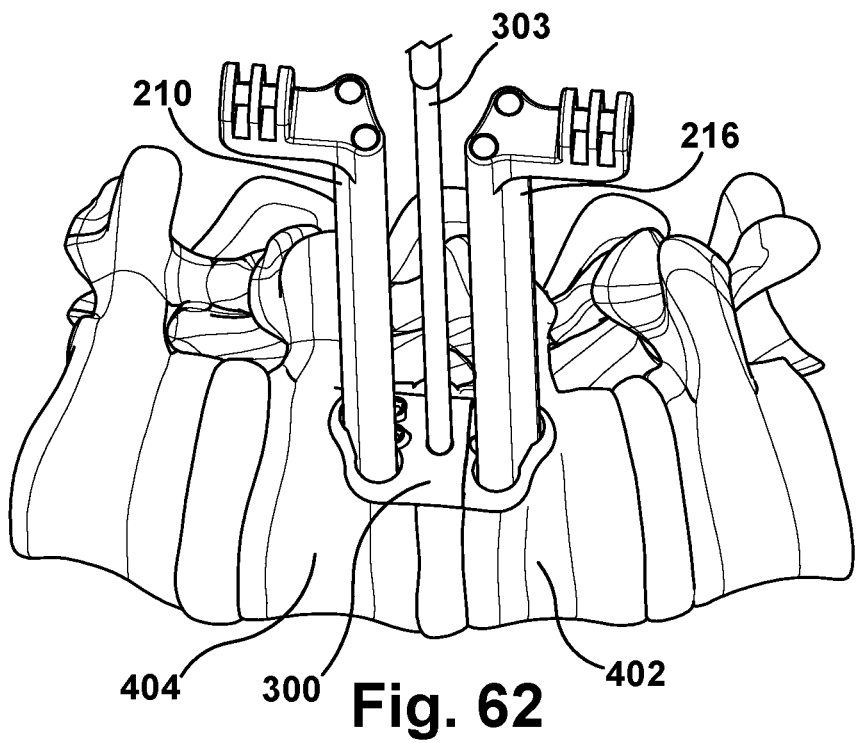

Referring to FIG. 61, disc space 602 optionally can be compressed. To do so, orthopedic instrument 200 can be slide over the posterior guide pins 403c and 403d. In particular, posterior cannula 210 of first guide 206 can slide over guide pin 403c and posterior cannula 216 of second guide 212 can be slide over guide pin 403d. Orthopedic instrument then can be adjusted to compress disc space 602 as depicted in FIG. 62 by using the control device (not shown) to slide first arm 204 towards from second arm 205, for example. As compression force is being applied to vertebrae 402 and 404, locking screw 301 of bone plate assembly can be tightened with a driver 303, as depicted in FIG. 62, thereby preserving and maintaining the compression load applied to vertebrae 402 and 404. In particular, the tightened lock screw 301 preserves the compression of the disc space 602 after the compression force applied by orthopedic instrument 200 is removed.

Figure 63:
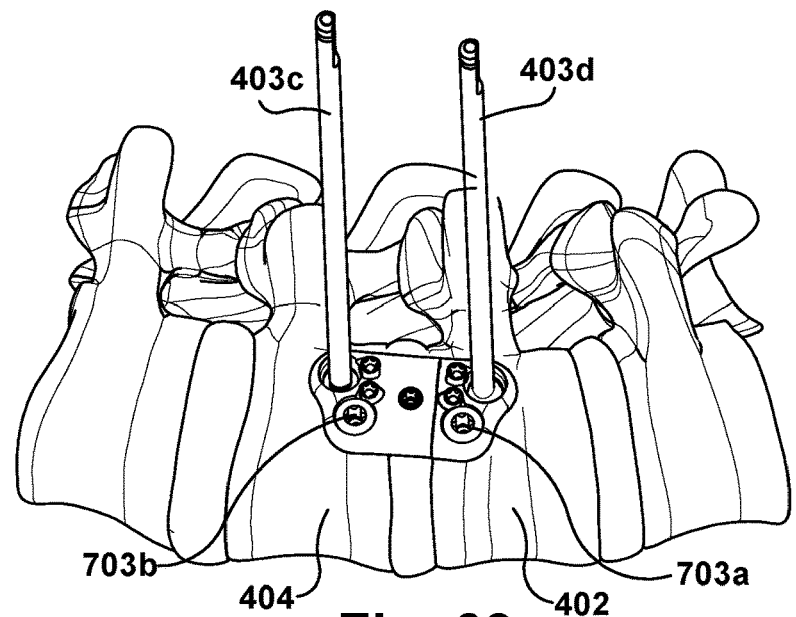
Figure 64:
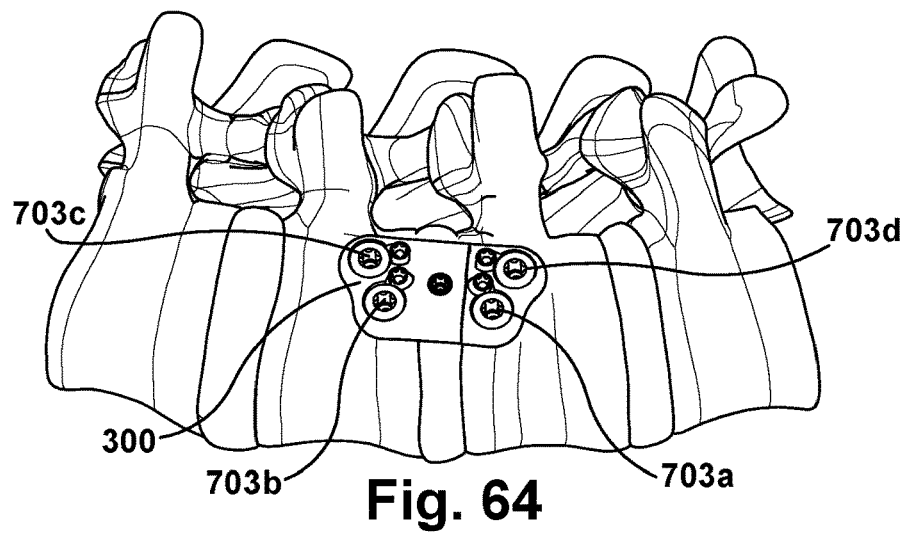
Figure 65:
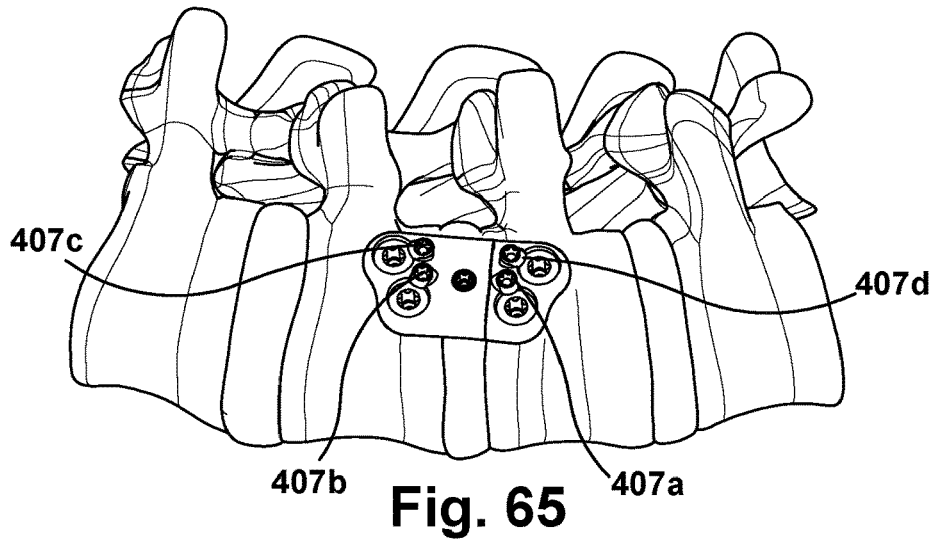

Referring to FIG. 63, after the compression force applied by orthopedic instrument 200 is released, orthopedic instrument 200 can be removed. Posterior guide pins 403c and 403d can be removed and bone screws 703c and 703d can be inserted into the holes created by posterior guide pins 403c and 403d as illustrated in FIG. 64. Referring to FIG. 65, in embodiments of an expandable bone plate assembly including bone screw locks, the bone screw locks 407 can be rotated over the bone screws 703 as depicted in FIG. 64. The same instrument used to tightened lock screw 301 can be used to rotate bone screw locks 407 over bone screws 703.

The above-described methods allow disc space between adjacent vertebrae to be distracted and optionally compressed using pins inserted into adjacent vertebrae. The same pins can be used to guide placement of an expandable bone plate assembly onto the vertebrae. Since such methods are used with an expandable bone plate assembly, the bone plate assembly can be expanded and slide over the inserted pins without requiring the pins to be spaced an exact length across the disc space. After the bone plate assembly is in place, the pins can be removed and replaced with bone screws. Such steps facilitate plate and screw placement.

Figure 66:
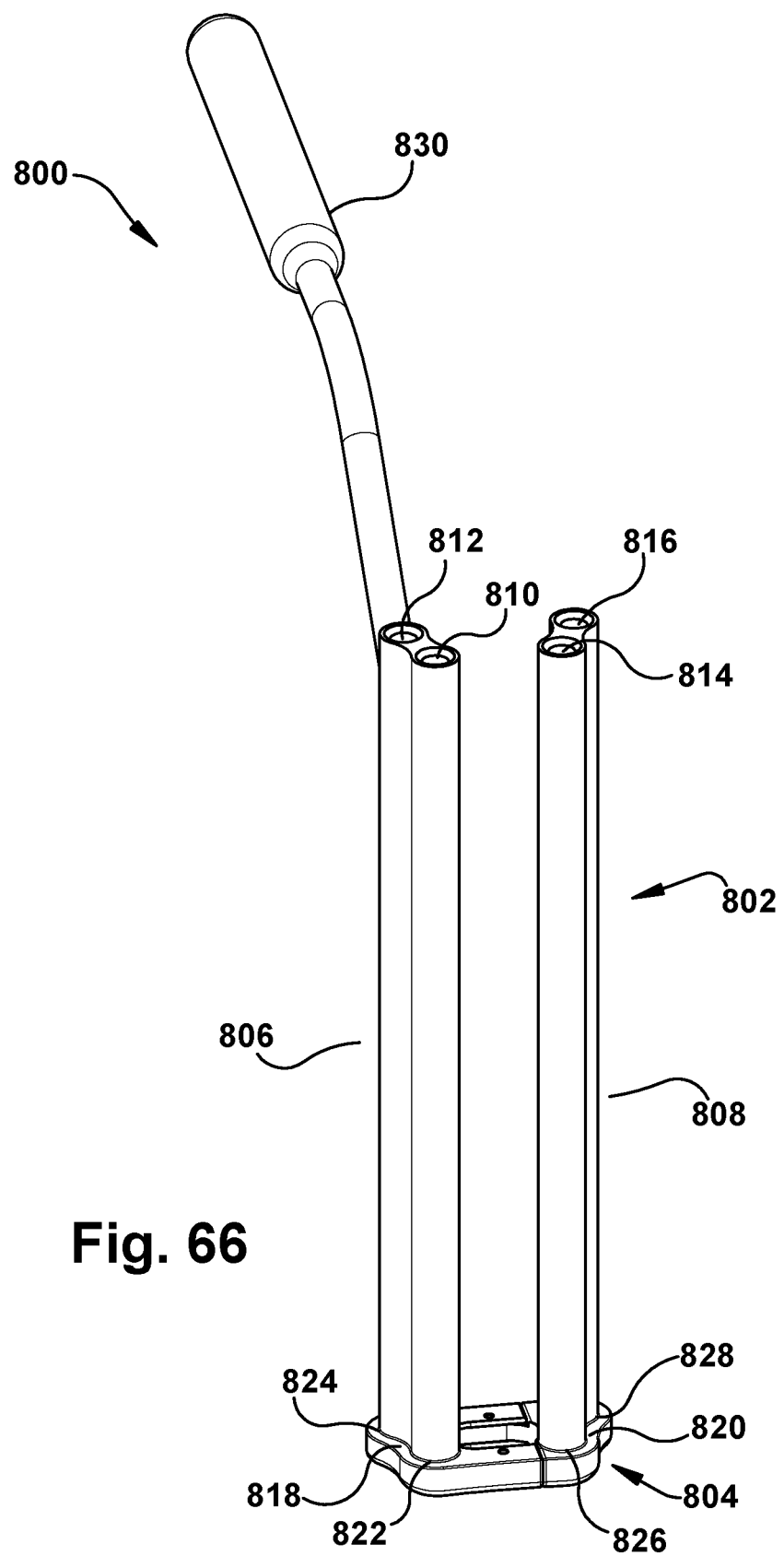

FIGS. 66-70 illustrate steps and devices of another embodiment of a method of implanting an expandable bone plate assembly without distracting adjacent vertebrae. Such a method involves using an orthopedic instrument including a bone plate template. Such an orthopedic instrument 800 is depicted in FIG. 66 and comprises a guide 802 having a distal end comprising an expandable plate template 804. In particular, guide 802 comprises a first guide portion 806 and a second guide portion 808. First guide portion 806 comprises an anterior cannula 810 and a posterior cannula 812. Similarly, second guide portion 808 comprises an anterior cannula 814 and a posterior cannula 816. Expandable plate template 804 comprises a first plate template portion 818 slidably attached to a second plate template portion 820. First plate template portion 818 comprises an anterior hole 822 axially aligned with and in fluid communication with anterior cannula 810 of first guide portion 806 and a posterior hole 824 axially aligned with and in fluid communication with posterior cannula 812 of first guide portion 806. Second plate template portion 820 comprises an anterior hole 826 axially aligned with and in fluid communication with anterior cannula 814 of second guide portion 808 and a posterior hole 828 axially aligned with and in fluid communication with posterior cannula 816 of second guide portion 808. Orthopedic instrument 800 further includes a handle 830 extending proximally from plate template 804. Kits of the present disclosure can include orthopedic instruments having plate templates that slide apart the same distance as a corresponding expandable bone plate assembly of such a kit.

Figure 67:
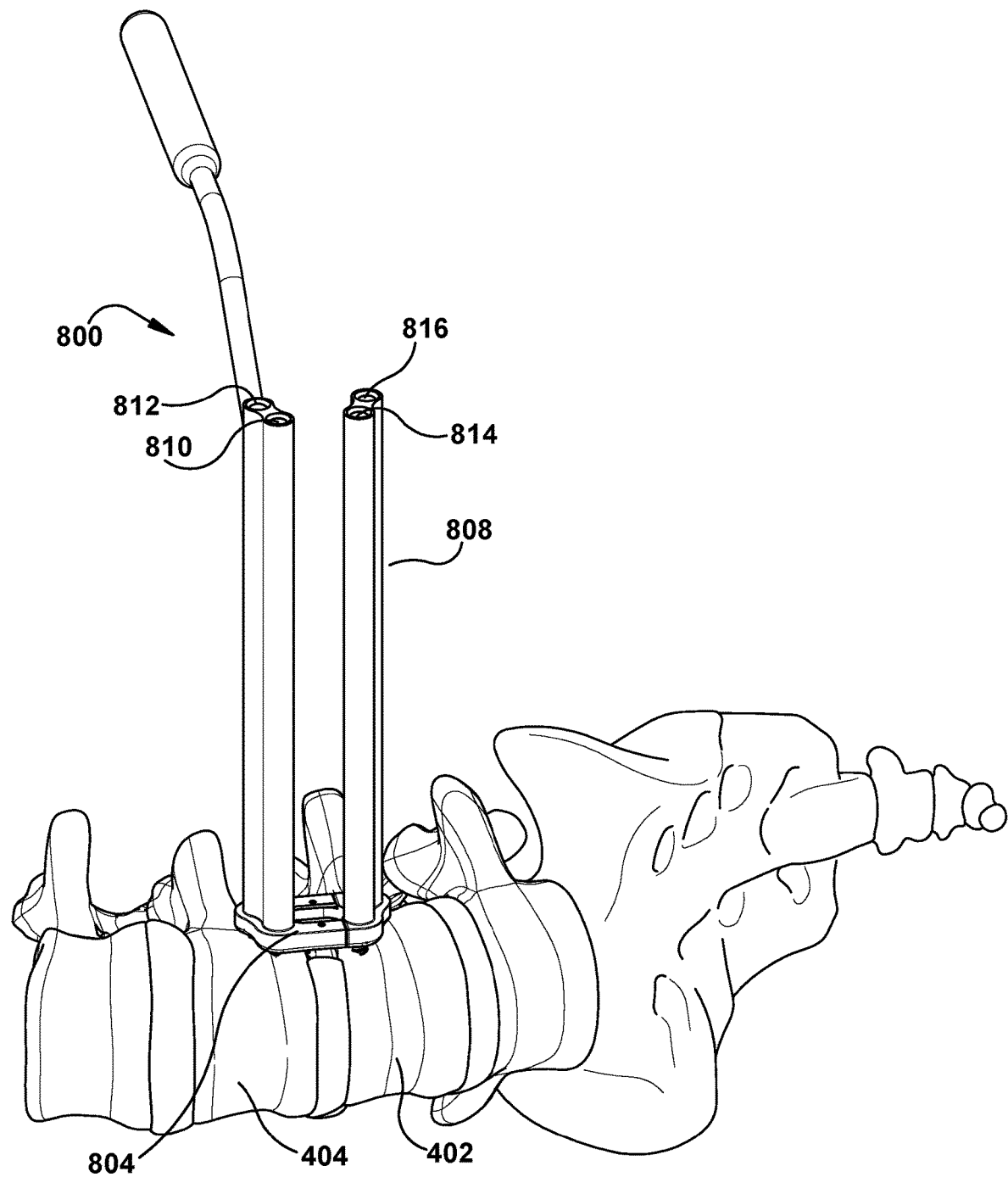
Figure 68:
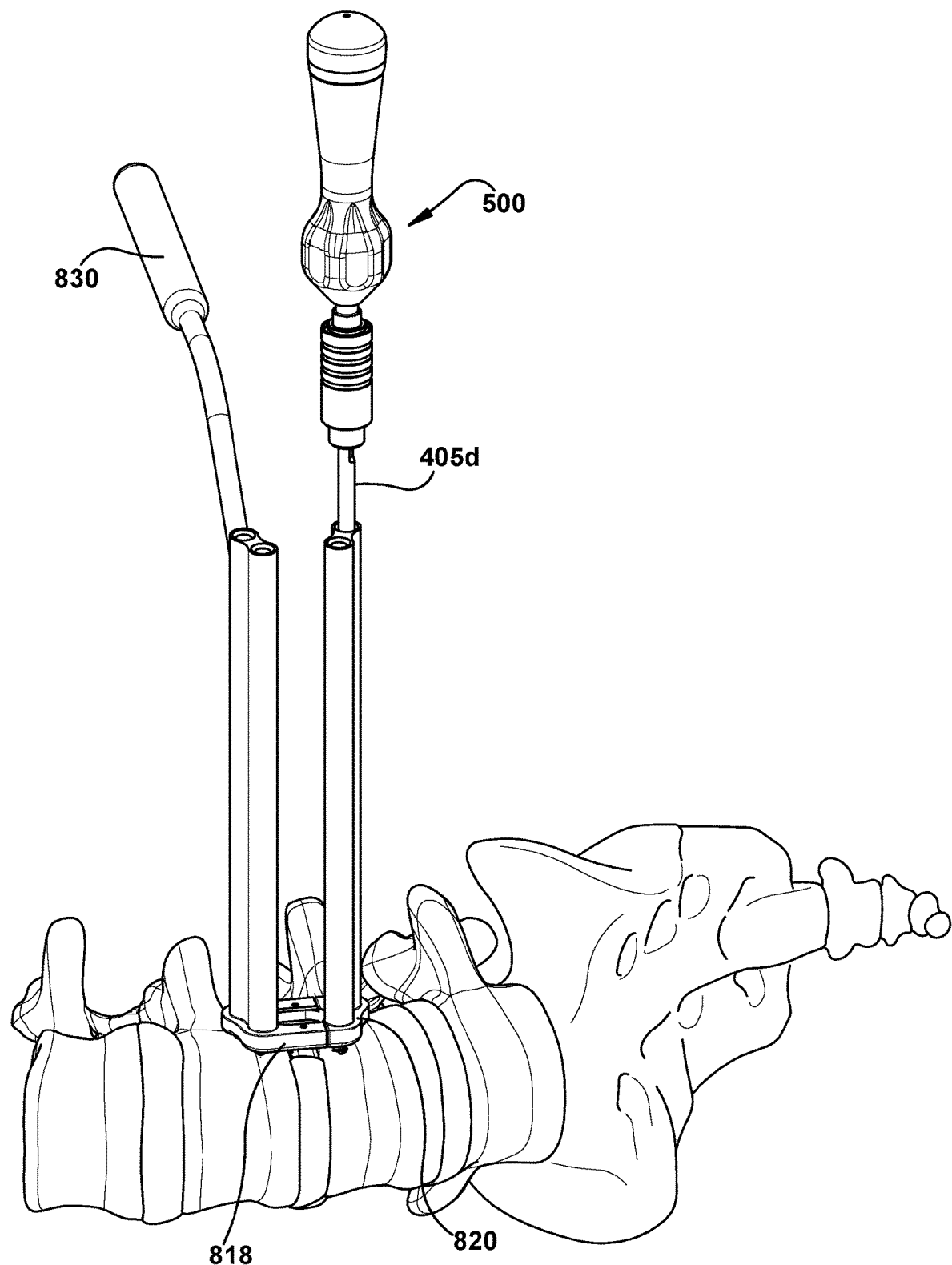
Figure 69:
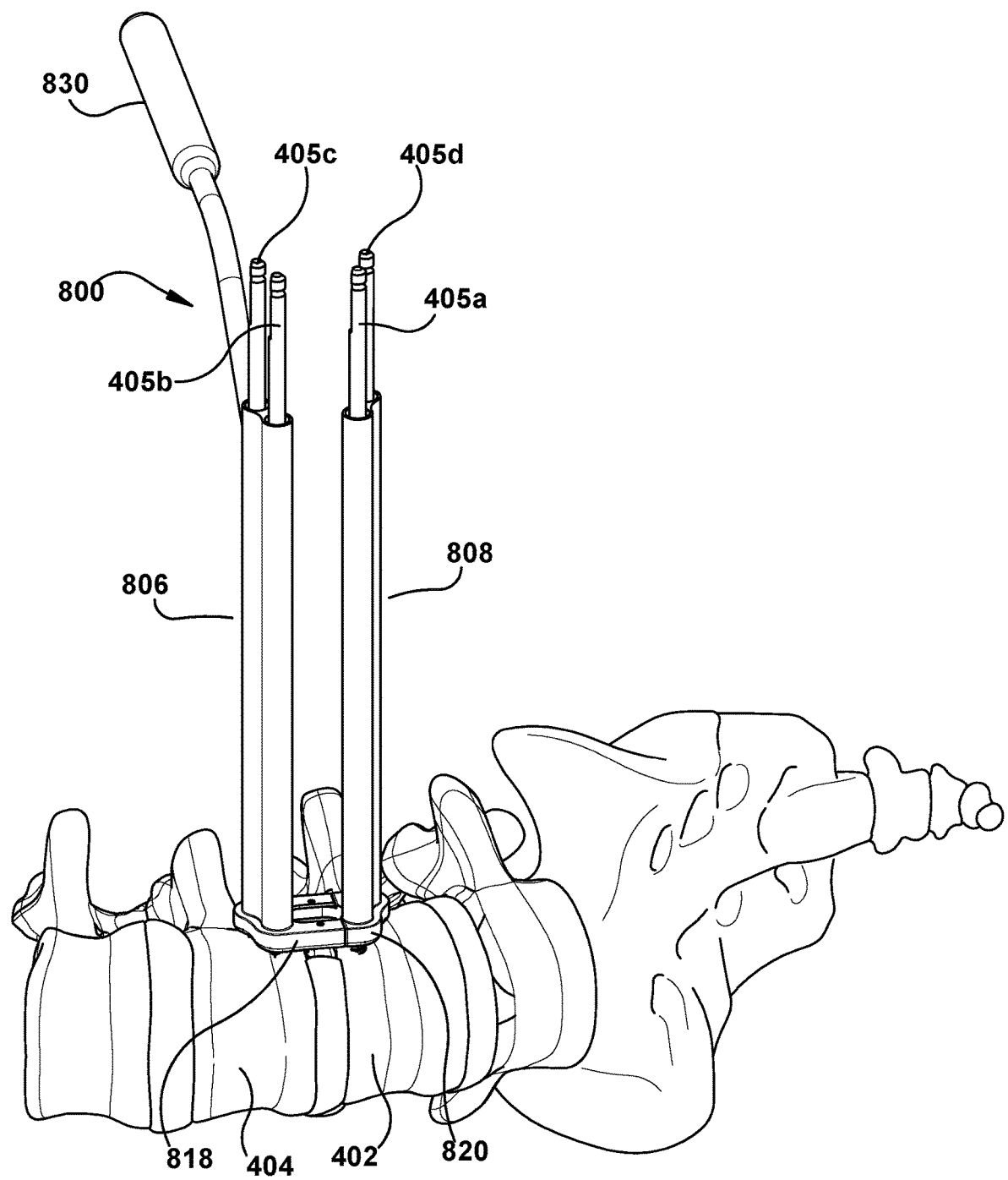
Figure 70:
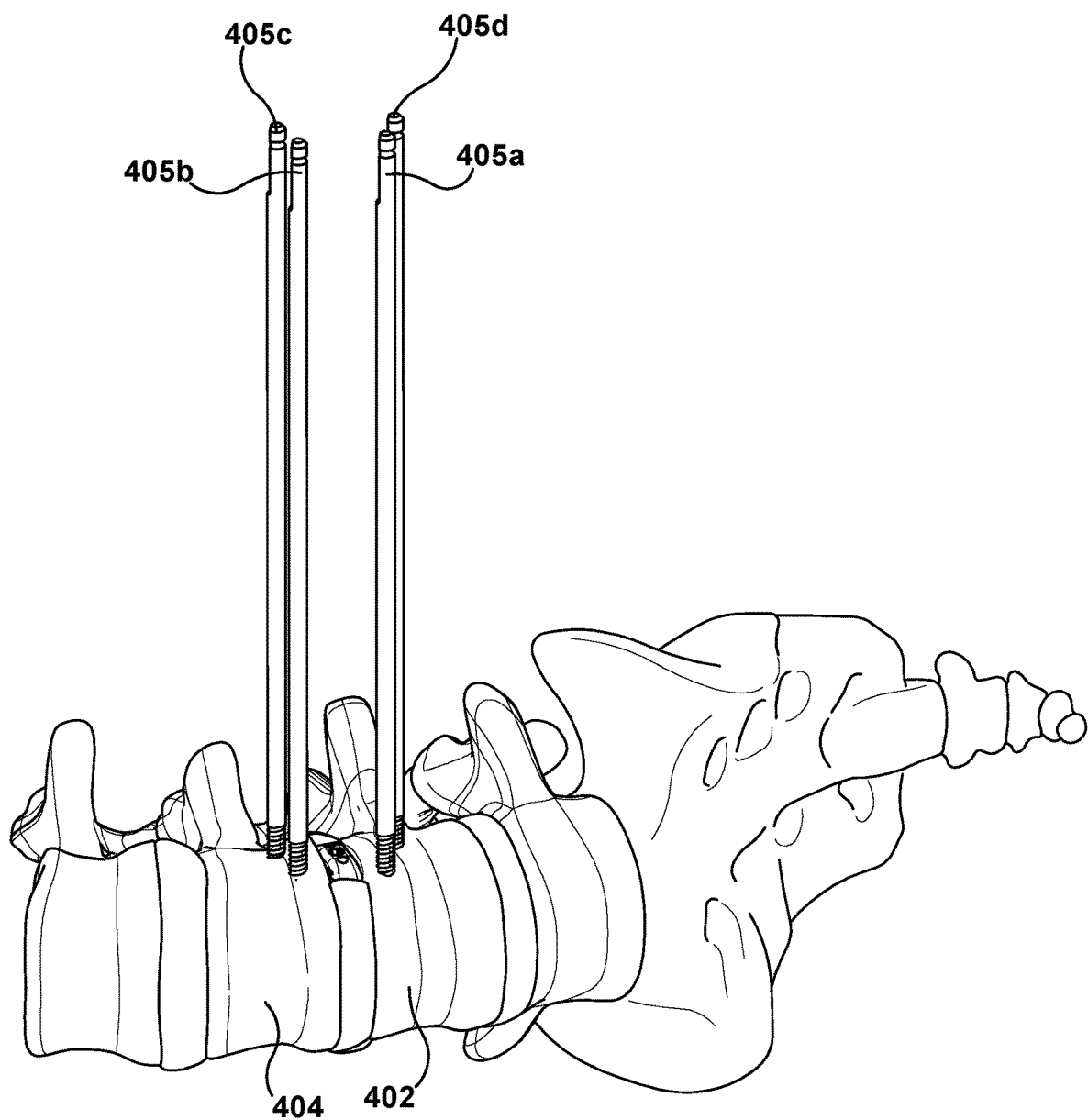

Referring to FIGS. 67 and 68, bone plate template 804 can be placed against vertebra 404 and 402 and pins 405a (not shown) and 405d can be respectively inserted into anterior cannula 814 and posterior cannula 816 of second guide portions 808 using pin inserter 500. Referring to FIG. 69, handle 830 can be used to slide first plate template portion 818 and second plate template portion 820 apart to position the second set of guide pins 405b and 405c, which can be respectively inserted into anterior cannula 810 and posterior cannula 812 of first guide portion 806. Orthopedic instrument 800 then can be removed leaving pins 405 positioned in vertebra 402 and 404 as seen in FIG. 70. The pins can be removed and an expandable plate can be secured to vertebrae 402 and 404 as described above.

It should be noted that the terms "anterior" and "posterior" as described with respect to the cannulas of the orthopedic instrument, the pins, and the bone screw holes of the expandable plate assembly are only used for the sake of clarity in describing a lateral interbody fusion procedure and with reference to FIGS. 33-70. Such terms do not necessarily correspond to standard anatomical positions as they relate to other orthopedic procedures, such as an anterior lumbar interbody fusion procedure, for example.

Expandable bone plate assemblies as disclosed herein can be used for bone fractures, bone fusion, and other medical procedures requiring fixation of tissue. Such devices can be configured to be implanted on the spinal column, such as, for example, the cervical spinal region, the lumbar spinal region or the sacral spinal region. The devices also can be configured as occipito-cervico-thoracic fixation devices to treat pathologies of the occipitocervical junction, and the posterior cervical and upper thoracic spine. Alternatively, bone plate assemblies can be configured to stabilize skull fractures, facial fractures, or craniomaxillofacial fractures. The bone plate assemblies can be left in place in the patient or removed after the bone has fused.

In certain embodiments, a bone plate assembly can be used as a supplemental fixation device and can be part of a kit of bone plate assemblies of a variety of shapes and sizes of one-level lumbar and sacral plates assemblies and screws. Bone plate assemblies can attach to the lumbar and lumbosacral spine (L1-S1). Bone plate assemblies can be implanted via a lateral or anterolateral surgical approach above the bifurcation of the great vessels in the treatment of the lumbar spine (L1-L5) or via an anterior approach below the bifurcation of the great vessels in the treatment of the lumbar and the lumbosacral spine (L1-S1). A bone plate assembly can provide immobilization and stabilization as an adjunct to fusion in skeletally mature patients in the treatment of, for example, fracture (including dislocation and subluxation); tumor; degenerative disc disease (defined as back pain of discogenic origin with degeneration of the disc confirmed by patient history and radiographic studies); pseudoarthrosis; spondylolysis; spondylolisthesis; scoliosis; lordotic deformities of the spine; spinal stenosis; and/or failed previous spine surgery Each of the disclosed aspects and embodiments of the present disclosure may be considered individually or in combination with other aspects, embodiments, and variations of the disclosure. Further, while certain features of embodiments of the present disclosure may be shown in only certain figures, such features can be incorporated into other embodiments shown in other figures. Unless otherwise specified, none of the steps of the methods of the present disclosure are confined to any particular order of performance.

What is claimed is:

1. A method of implanting an expandable bone plate against adjacent first and second vertebrae comprising:
   obtaining an expandable bone plate comprising a first plate portion slidably attached to a second plate portion, the first and second plate portions collectively comprising a plurality of bone screw holes;
   inserting a plurality of guide pins into a first vertebra and a second vertebra;
   distracting the space between the first vertebra and the second vertebra using an orthopedic instrument coupled to the guide pins;

disengaging the guide pins from the orthopedic instrument;
adjusting the size of the expandable plate, if necessary, so that the plurality of bone screw holes of the first and second plate portions are aligned with the plurality of guide pins;
placing the plurality of bone screw holes in the expandable plate about respective ones of the plurality of guide pins such that the guide pins extend through the plurality of bone screw holes;
seating the expandable bone plate against the first vertebra and the second vertebral translating the expandable bone plate along the guide pins until the expandable bone plate contacts the first vertebra and the second vertebra;
removing the plurality of guide pins from the first vertebra and the second vertebra; and
inserting a bone screw into each of the plurality of bone screw holes of the first plate portion and the second plate portion.

2. The method of claim 1, wherein the plurality of bone screw holes comprises an anterior bone screw hole and a posterior bone screw hole defined by the first plate portion and an anterior bone screw hole and a posterior bone screw hole defined by the second bone plate portion.

3. The method of claim 2, further comprising obtaining an adjustable orthopedic instrument comprising:
a first guide comprising an anterior cannula axially alignable with the anterior bone screw hole of the first plate portion and a posterior cannula axially alignable with the posterior bone screw hole of the first plate portion; and
a second guide comprising an anterior cannula axially alignable with the anterior bone screw hole of the second plate portion and a posterior cannula axially alignable with the posterior bone screw hole of the second plate portion.

4. The method of claim 3, wherein inserting a plurality of guide pins into a first vertebra and a second vertebra comprises:
inserting one of the plurality of guide pins into a location of the first vertebra or the second vertebra;
placing one of the cannulas of either the first guide or the second guide of the adjustable orthopedic instrument about the one of the plurality of guide pins;
adjusting the distance between the first and second guides to set the location for insertion of the remaining ones of the plurality of guide pins;
inserting the remaining ones of the plurality of pins through respective remaining ones of the cannulas of the adjustable orthopedic instrument and into the first vertebra and the second vertebra.

5. The method of claim 4, wherein inserting one of the plurality of guide pins into a location of the first or the second vertebrae comprises inserting the one of the plurality of guide pins into an anterior location of the first vertebra or the second vertebra and wherein inserting the remaining ones of the plurality of guide pins into the first and the second vertebra comprises inserting a posterior guide pin through the posterior cannula of the first guide into a posterior location of the first vertebra and inserting a posterior guide pin through the posterior cannula of the second guide into a posterior location of the second vertebra after distracting the space between the first and the second vertebra.

6. The method of claim 4, wherein the same adjustable orthopedic instrument is used to adjust the distance between the first and second guides and to distract the space between the first and the second vertebra.

7. The method of claim 4, wherein the distance between the first and second guides is adjustable and the distance between the anterior and posterior cannulas of each of the first and second guides is fixed.

8. A method of implanting an expandable bone plate against adjacent first and second vertebrae comprising:
inserting one of a plurality of guide pins into a desired location of a first vertebra;
obtaining an orthopedic instrument comprising a first guide and a second guide, each guide having a plurality of cannulas;
placing one of the plurality of cannulas of the first or second guide about the one of the plurality of guide pins;
adjusting the orthopedic instrument to adjust the relative position of the first and second guides to set the location of the remaining ones of the plurality of guide pins for insertion into the first vertebra and a second vertebra;
inserting the remaining ones of the plurality of guide pins into the respective remaining ones of the plurality of cannulas of the first and second guide and into locations of the first vertebra and the second vertebrae;
distracting the disc space between the first vertebra and the second vertebra using the orthopedic instrument;
disengaging the guide pins from the orthopedic instrument;
inserting an interbody device into the disc space;
obtaining an expandable bone plate comprising a first plate portion slidably attached to a second plate portion, the first and second plate portions collectively comprising a plurality of bone screw holes, the expandable bone plate further comprising a locking screw mounted on the first plate portion;
adjusting the size of the expandable bone plate, if necessary, so that the plurality of bone screw holes of the first and second plate portions are aligned with the plurality of guide pins;
placing the plurality of bone screw holes in the expandable plate about respective ones of the plurality of guide pins such that the guide pins extend through the plurality of bone screw holes;
translating the expandable bone plate along the guide pins until the expandable bone plate contacts the first vertebra and the second vertebra;
removing the plurality of guide pins; and
inserting a bone screw through each of the plurality of bone screw holes of the expandable bone plate and through the holes created by the plurality of guide pins to seat the expandable bone plate against the first vertebra and the second vertebra.

9. The method of claim 8, wherein the guide pins all have substantially the same length.

10. The method of claim 8, wherein the first guide comprises an anterior cannula and a posterior cannula and the second guide comprises an anterior cannula and a posterior cannula.

11. The method of claim 10, wherein inserting the remaining ones of the plurality of guide pins comprises:
inserting a posterior guide pin through the posterior cannula of the first guide into a posterior location of the first vertebra; and
inserting a posterior guide pin through the posterior cannula of the second guide into a posterior location of the second vertebra, wherein the posterior guide pins are inserted after distracting the disc space between the first and the second vertebra.

12. The method of claim 11, wherein removing the plurality of guide pins and inserting the bone screw comprises:
removing an anterior guide pin from an anterior location of the first vertebra creating an anterior hole in the first vertebra;
removing an anterior guide pin from an anterior location of the second vertebra creating an anterior hole in the second vertebra;
inserting an anterior bone screw into the anterior hole of the first vertebra; and inserting an anterior bone screw hole into the anterior hole of the second vertebra.

13. The method of claim 12, further comprising:
placing the posterior cannula of the first guide and the posterior cannula of the second guide about the respective posterior guide pin;
compressing the disc space while tightening the locking screw so that the locking screw contacts the second plate portion to preserve compression after the compression force applied by the orthopedic instrument is released;
releasing the compression force from the orthopedic instrument; removing the posterior guide pins creating posterior holes in the first and the second vertebra; inserting a bone screw into each of the posterior holes; and rotating a screw locking rivet over the bone screw.

14. A method of implanting an expandable bone plate against adjacent first and second vertebra comprising:
inserting one of a plurality of guide pins into a desired location of a first vertebra;
obtaining an orthopedic instrument comprising a first guide and a second guide, each guide having a plurality of cannulas;
aligning the first and second guides of the orthopedic instrument so that one of the plurality of cannulas of the first or second guide is disposed about the one of the plurality of guide pins and a distal end of the orthopedic instrument is contacting the first vertebra and a second vertebra;
inserting the remaining ones of the plurality of guide pins into the respective remaining ones of the plurality of cannulas of the first and second guide and into locations of the first vertebra and the second vertebrae;
distracting the disc space between the first vertebra and a second vertebra using the orthopedic instrument;
disengaging the guide pins from the orthopedic instrument;
inserting an interbody device into the disc space;
obtaining an expandable bone plate comprising a first plate portion slidably attached to a second plate portion, the first and second plate portions collectively comprising a plurality of bone screw holes;
adjusting the size of the expandable bone plate, if necessary, so that the plurality of bone screw holes of the first and second plate portions are aligned with the plurality of guide pins;
placing the plurality of bone screw holes in the expandable plate about respective ones of the plurality of guide pins such that the guide pins extend through the plurality of bone screw holes;
translating the expandable bone plate along the guide pins until the expandable bone plate contacts the first vertebra and the second vertebra;
removing the plurality of guide pins; and
inserting a bone screw through each of the plurality of bone screw holes of the expandable bone plate and through the holes created by the plurality of guide pins to seat the expandable bone plate against the first vertebra and the second vertebra.

15. A method of implanting a bone plate against a first vertebra and a second vertebra comprising:
obtaining an orthopedic instrument comprising:
a guide comprising a first guide portion and a second guide portion, the first guide portion comprising an anterior cannula and a posterior cannula, the second guide portion comprising an anterior cannula and a posterior cannula; and
an expandable plate template attached to the distal end of the guide, the expandable plate template comprising: a first plate template portion comprising an anterior hole axially aligned with and in fluid communication with the anterior cannula of the first guide portion and a posterior hole axially aligned with and in fluid communication with the posterior cannula of the first guide portion;
a second plate template portion slidably attached to the first plate template portion and comprising an anterior hole axially aligned with and in fluid communication with the anterior cannula of the second guide portion and a posterior hole axially aligned with and in fluid communication with the posterior cannula of the second guide portion; and
a handle extending proximally from the expandable plate template;
placing the expandable plate template against a first vertebra;
inserting respective ones of a plurality of guide pins into the anterior cannula and the posterior cannula of the second guide portion into the first vertebra;
sliding the first plate template portion away from the second plate template portion set the location of insertion of additional guide pins in the first vertebra and the second vertebra;
inserting respective ones of the additional guide pins into the anterior cannula and the posterior cannula of the first guide portion into the second vertebra;
removing the orthopedic instrument from the first and the second vertebra leaving the plurality of guide pins in the first vertebra and the second vertebra;
sliding an expandable plate over the plurality of guide pins by translating the expandable bone plate along the guide pins until the expandable bone plate contacts the first vertebra and the second vertebra and thereby seat the expandable plate against the first and the second vertebra; and
removing the plurality of guide pins.

* * * * *